United States Patent [19]

Jacquet et al.

[11] Patent Number: 5,196,189

[45] Date of Patent: Mar. 23, 1993

[54] QUATERNIZED POLYMER FOR USE AS A COSMETIC AGENT IN COSMETIC COMPOSITIONS FOR THE HAIR AND SKIN

[75] Inventors: Bernard Jacquet, Antony; Gerard Lang, Deuil-La-Barre, both of France

[73] Assignee: Societe Anonyme dite: L'Oreal, Paris, France

[21] Appl. No.: 897,483

[22] Filed: Jun. 12, 1992

Related U.S. Application Data

[60] Continuation of Ser. No. 527,948, Apr. 23, 1990, abandoned, which is a division of Ser. No. 545,770, Oct. 26, 1983, Pat. No. 4,948,579, which is a division of Ser. No. 163,411, Jun. 26, 1980, Pat. No. 4,422,853, which is a continuation-in-part of Ser. No. 849,667, Nov. 8, 1977, Pat. No. 4,148,370, which is a continuation-in-part of Ser. No. 577,836, May 15, 1975, abandoned.

[30] Foreign Application Priority Data

May 16, 1974 [LU] Luxembourg ............ 70096
Feb. 14, 1975 [LU] Luxembourg ............ 71849

[51] Int. Cl.$^5$ ............................................. A61K 7/09
[52] U.S. Cl. ............................ 424/72; 514/845; 514/846
[58] Field of Search ................... 424/72; 514/845, 846

[56] References Cited

U.S. PATENT DOCUMENTS

| | | | |
|---|---|---|---|
| 2,227,378 | 1/1942 | Searle | 424/72 |
| 3,270,022 | 8/1966 | Wakeman et al. | 424/72 |
| 3,322,676 | 6/1967 | Hiestand | 424/72 |
| 3,370,048 | 2/1968 | Reynolds | 424/72 |
| 3,530,215 | 9/1970 | Grief et al. | 424/72 |
| 3,663,461 | 5/1972 | Witt | 424/72 |
| 3,778,476 | 12/1973 | Rembaum et al. | 424/72 |
| 3,986,825 | 10/1976 | Sokol | 424/72 |
| 4,009,255 | 2/1977 | Kalopissis et al. | 424/72 |
| 4,134,411 | 1/1979 | Yamazaki | 424/72 |
| 4,150,115 | 4/1979 | Jacquet et al. | 424/72 |
| 4,197,865 | 4/1980 | Jacquet et al. | 424/72 |
| 4,217,914 | 8/1980 | Jacquet et al. | 132/7 |
| 4,422,853 | 12/1983 | Jacquet et al. | 8/406 |
| 4,948,579 | 8/1990 | Jacquet et al. | 424/72 |

FOREIGN PATENT DOCUMENTS

2514640 4/1983 France .
2068031 1/1980 United Kingdom .

*Primary Examiner*—Frederick E. Waddell
*Assistant Examiner*—Frederick F. Tsung
*Attorney, Agent, or Firm*—Cushman, Darby & Cushman

[57] ABSTRACT

A quaternized polymer for use as a cosmetic agent, has recurring units of the formula $$-\overset{R}{\underset{R'}{N^{\oplus}}}-A-\overset{R}{\underset{R'}{N^{\oplus}}}-B-\quad X^{\ominus}\ X^{\ominus}$$

wherein
R is lower alkyl or $-CH_2-CH_2OH$;
R' is an aliphatic, alicyclic or arylaliphatic radical containing a maximum of 20 carbon atoms, or R and R' together with the nitrogen atom to which they are attached form a heterocycle capable of containing a heteroatom other than nitrogen;
A is a divalent group selected from o-, m- or p-xylylidene of the formula (1)

$$-CH_2-\underset{}{\underset{}{\bigcirc}}-CH_2-$$

$$-(CH_2)_y-\underset{E}{CH}-(CH_2)_x-\underset{K}{CH}-(CH_2)_t- \quad (2)$$

wherein x, y and t are whole numbers ranging from 0 to 11 such that the sum (x+y+t) is greater than or equal to 0 and lower than 18, and E and K represent hydrogen or an aliphatic radical having less than 18 carbon atoms, $$-(CH_2)_n-S-(CH_2)_n-, \quad (3)$$

$$-(CH_2)_n-O-(CH_2)_n-, \quad (4)$$

$$-(CH_2)_n-S-S-(CH_2)_n-, \quad (5)$$

$$-(CH_2)_n-SO-(CH_2)_n-, \quad (6)$$

$$-(CH_2)_n-SO_2-(CH_2)_n-\text{and} \quad (7)$$

$$-\underset{}{\bigcirc}-CH_2-\underset{}{\bigcirc}- \quad (8)$$

wherein n is equal to 2 or 3;
B represents a divalent group selected from o-, m- or p-xylylidene of the formula (1)

(Abstract continued on next page.)

-continued

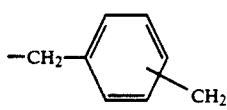

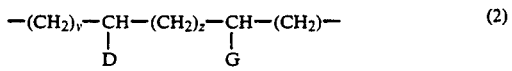

wherein D and G represent hydrogen or an aliphatic radical having less than 18 carbon atoms and v, z and u are whole numbers ranging from 0 to 11, with two of v, z and u simultaneously being capable of being 0, such that the sum (v+z+u) is greater than or equal to 1 and lower than 18 and such that the sum (v+z+u) is greater than 1 when the sum (x+y+t) is equal to 0,

wherein n is 2 or 3; and $X^{\ominus}$ is an anion derived from an organic or mineral acid. The quaternized polymer is employed in cosmetic compositions for the hair and skin.

24 Claims, No Drawings

QUATERNIZED POLYMER FOR USE AS A COSMETIC AGENT IN COSMETIC COMPOSITIONS FOR THE HAIR AND SKIN

This application is a continuation of Ser. No. 07/527,948 filed Apr. 23, 1990, now abandoned which is a divisional of Ser. No. 06/545,770 filed Oct. 26, 1983, now U.S. Pat. No. 4,948,579, which is a divisional of Ser. No. 06/163,411 filed Jun. 26, 1980, now U.S. Pat. No. 4,422,853 which is a continuation-in-part of our application Ser. No. 849,667, filed Nov. 8, 1977, which, in turn, is a continuation-in-part of our application Ser. No. 577,836, filed May 15, 1975, now abandoned.

The present invention relates to the use, in a cosmetic composition, of polymers possessing quaternized ammonium groups, to cosmetic compositions containing these polymers, and to a process for treating hair or the skin with said compositions.

The polymers of the present invention are, more particularly, cationic polymers having quaternized nitrogen atoms which are part of the macrochain.

Certain polymers of this type are known and have already been proposed for use as pesticidal agents, flocculation agents, surfactants or as ion exchange agents.

It has now surprisingly been discovered that such polymers exhibit interesting cosmetic characteristics when they are incorporated into compositions which are applied to the hair or skin.

One embodiment of the present invention relates to the use as a cosmetic agent, and principally to the use in the preparation of cosmetic compositions, of quaternized polymers having recurrings units of formula I $$
\overset{R}{\underset{R'}{-\overset{|}{N}^{\oplus}}}-A-\overset{R}{\underset{R'}{\overset{|}{N}^{\oplus}}}-B \quad X^{\ominus} \quad X^{\ominus} \quad (I)
$$

wherein $X^{\ominus}$ represents an anion derived from a mineral or organic acid;

R is lower alkyl or —CH$_2$—CH$_2$—OH;

R' is an aliphatic, alicyclic or an arylaliphatic radical, containing a maximum of 20 carbon atoms; R and R' together with the nitrogen atom to which they are attached can form a ring capable of containing a second heteroatom other than nitrogen;

A represents a divalent group of the formula

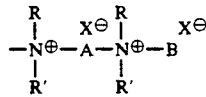—CH$_2$—, (o-, m- or p-) or

—(CH$_2$)$_y$—CH—(CH$_2$)$_x$—CH—(CH$_2$)$_t$—
        |                      |
        E                      K wherein x, y and t are whole numbers ranging from 0 to 11 and such that the sum (x+y+t) is greater than or equal to 0 and lower than 18, and E and K represent hydrogen or an aliphatic radical having less than 18 carbon atoms. A can also represent a divalent group of the formula:

—(CH$_2$)$_n$—S—(CH$_2$)$_n$—,

—(CH$_2$)$_n$—O—(CH$_2$)$_n$—,

—(CH$_2$)$_n$—S—S—(CH$_2$)$_n$—,

—(CH$_2$)$_n$—SO—(CH$_2$)$_n$—,

—(CH$_2$)$_n$—SO$_2$—(CH$_2$)$_n$— or

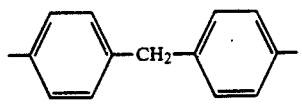—CH$_2$—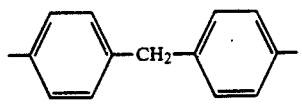

wherein n is a whole number equal to 2 or 3; and B represents a divalent group of the formula $$
-CH_2-\overset{OH}{\underset{|}{CH}}-CH_2- \text{ or } -(CH_2)_n-O-(CH_2)_n
$$

wherein n has the meaning given above.

As indicated above, certain polymers of formula I are known while others are new.

In that which follows and for the sake of simplicity, polymers whose recurring units correspond to formula I will be designated by the expression "polymers of formula I".

The terminal groups of polymers of formula I can vary with the amount of initial reactants employed to produce the same. They can be either of the type $$
\overset{R}{\underset{R'}{\diagdown}} N-A- \text{ or of the type } X-B-.
$$

In formula I, X⁻ represents principally a halide anion such as bromide, iodide or chloride, or an anion derived from other mineral acids, such as phosphoric acid, sulfuric acid and the like, or even an anion derived from an organic sulfonic or carboxylic acid, principally an alkanoic acid having 2-12 carbon atoms, for example, acetic acid, a phenylalkanoic acid, for example, phenylacetic acid, benzoic acid, lactic acid, citric acid or paratoluene sulfonic acid. The substituent R represents, preferably, an alkyl group having from 1 to 6 carbon atoms. When R' represents an aliphatic radical, the same generally is alkyl or cycloalkyl wherein the alkyl has less than 20 carbon atoms and preferably not more than 16 carbon atoms. When R' represents an alicyclic radical, the same generally is cycloalkyl having 5 or 6 chains. When R' represents an arylaliphatic radical, the same generally is aralkyl such as phenylalkyl wherein the alkyl moiety has, preferably, 1-3 carbon atoms. When both R and R' and the nitrogen atom to which they are attached form a ring, R and R' can represent together, principally, a polymethylene radical having 2 to 6 carbon atoms, and the ring can include a second heteroatom, such as oxygen or sulfur. When the substituents E, K, D or G are an aliphatic radical, they generally are an alkyl having from 1 to 17 carbon atoms and preferably 1 to 12 carbon atoms; v, z and u represent, preferably, numbers ranging from 1 to 5. Two of them, of course, can be equal to zero; x, y and t are preferably numbers ranging from 0 to 5. When A or B represents a xylylidene radical it can be an o-, m- or p-xylylidene group.

Among the polymers of formula I, those compounds which preferably are employed for cosmetic use according to the present invention are, notably, those for which R is methyl or hydroxyethyl; R' is alkyl having 1-16 carbon atoms or benzyl or cyclohexyl; or R and R' represent together —(CH$_2$)$_5$— or —(CH$_2$)$_2$—O—(CH$_2$)$_2$—; A is xylylidene or a polymethylene having 2-12 carbon atoms, optionally branched by one or two alkyl substituents having 1-12 carbon atoms, or

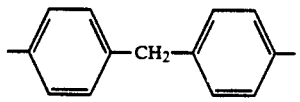

or a polymethylene having 4 or 6 carbon atoms and including a heteroatom group of the type —O—, —S—, —S—S—, —SO— or —SO$_2$—; B is a xylylidene radical or a polymethylene having 3 to 10 carbon atoms optionally branched by one or two alkyl substituents having 1-12 carbon atoms or

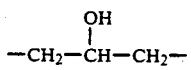

or a polymethylene radical having 4 or 6 carbon atoms and carrying an oxygen heteroatom; and X is chlorine or iodine or bromine.

It is to be understood that the invention also relates to the cosmetic use of polymers of formula I wherein A, B, R or R' have several different values in the same polymer I.

The preparation of such polymers is given in the following description and Example 43 is an illustration of the same.

The polymers of formula I can be prepared principally in accordance with the following procedures.

Process 1

This process comprises polycondensing a di-tertiary diamine of the formula

and a dihalide of the formula X-B$_1$-X, wherein R, R' and X have the meanings given above; A$_1$ represents A when B$_1$ represents B, and A$_1$ represents B when B$_1$ represents A, A and B being defined above.

This process for preparing polymers of formula I can be effected in accordance with one of the two following methods:

Process 1a

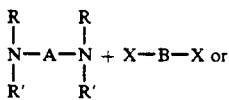

Process 1b

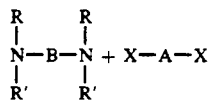

When A has one of the following values:

—(CH$_2$)$_n$—S—(CH$_2$)$_n$—,

—(CH$_2$)$_n$—SO—(CH$_2$)$_n$—,

—(CH$_2$)$_n$—SO$_2$—(CH$_2$)$_n$—,

—(CH$_2$)$_n$—S—S—(CH$_2$)$_n$— or

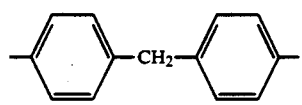

Process 1a is preferably employed.

For example, the polycondensation reaction is carried out in a solvent or in a mixture of solvents which favor a quaternization reaction. Such solvent(s) include water, dimethyl formamide, acetonitrile, lower alcohols, principally lower alkanols such as methanol, and the like.

The reaction temperature can range between 10° and 150° C., preferably between 20° and 100° C.

The reaction time can depend on such easily determined factors as the nature of the solvent employed, the initial reactants used as well as the degree of polymerization desired.

Generally, the initial reactants are employed in equimolar quantities, but it is possible to employ either the diamine or the dihalide in slight excess, this excess being lower than 20 mole percent.

The resulting polycondensate is isolated at the end of the reaction either by filtration or by concentrating the reaction mixture.

It is possible to regulate the average length and the polymer chain by adding, at the beginning, or during the course of the reaction, a small quantity, for instance, 1-15 mole percent relative to one of the initial reactants, of a monofunctional reactant such as a tertiary amine or a monohalide. In this case a portion, at least, of the terminal groups of the polymer I produced is constituted either by the tertiary amine group used, or by the hydrocarbon group of the monohalide employed. Some illustrations of limiting the length of the chain by the addition of variable quantities of triethylamine are given in Examples 47 to 49, below.

The present invention also relates to the cosmetic use of the polymers of formula I having such terminal groups.

There can also be employed as the initial reactants a mixture of di-tertiary diamines, or a mixture of dihalides, or even a mixture of di-tertiary amines and a mixture of dihalides with the proviso that the ratio of the total molar quantities of diamines and dihalides is near 1, as illustrated, for instance, in Example 43.

Process 2

This process comprises self-polycondensing a tertiary ω-halogenated amine of the formula

In this case, the polymer obtained corresponds to general formula I wherein B=A, and R, R' and X have the meanings given above except that A can only be

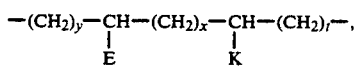

the sum (x+y+t) necessarily being in this case greater than 4.

This reaction can be conducted either in the absence of a solvent or with the same solvents as in Process 1 and by using the same reaction temperature ranges indicated therefor. As before, a monofunctional reactant can be added to the reaction medium to regulate the degree of polycondensation. Further, a mixture of several tertiary ω-halogenated amines can also be employed.

In the two processes for preparing the polymers of formula I mentioned above, the resulting polycondensate is isolated at the end of the reaction either by filtration, or by concentration of the reaction mixture and optional crystallization by the addition of an appropriate anhydrous organic liquid, for example, acetone.

The di-tertiary diamines used as initial reactants in Process 1, above, can be prepared in accordance with one of the methods given below.

Method 1

A primary amine of the formula R—NH$_2$ is reacted with a dihalide of the formula Hal—A$_1$—Hal, Hal being a halogen atom and preferably an atom of bromine or iodine. The reaction is carried out at a temperature between about 50° and 150° C. and an excess of primary amine is employed, i.e. generally 2 to 5 moles of primary amine per mole of dihalide are used. After treatment of the reaction mixture with a basic solution, for example, a solution of NaOH or KOH, a di-secondary diamine of the formula R—NH—A$_1$—NH—R is obtained. This latter product is then submitted to an alkylation reaction in accordance with conventional procedures, the expression "alkylation" meaning here the substitution of a hydrogen atom linked to the nitrogen by a R' group such as defined above. Then, in accordance with usual procedures, the di-tertiary diamine of the formula

is separated from the reaction mixture.

Method 2—applicable in the case wherein A$_1$ is a xylylidene or alkylene radical A primary amine of the formula R—NH$_2$ is reacted with an arylsulfonyl halide of the formula Ar—SO$_2$—Hal, Ar being an aryl group, for example, phenyl or tolyl, and Hal being a halogen, such as chlorine atom. A sulfonamide of the formula Ar—SO$_2$—NHR is obtained which is then submitted to an alkylation reaction in accordance with known procedures to form a sulfonamide of the formula

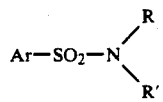

which, by acid hydrolysis employing for instance an aqueous sulfuric acid solution, procedures a secondary amine of the formula

This latter product is then reacted with a dihalide of the formula Hal—A$_1$—Hal, Hal and A being defined above in the presence of a tertiary amine such as N-ethyl diisopropylamine, by using at least two moles of secondary amine and tertiary amine per mole of dihalide. The reaction is carried out, preferably, in the absence of a solvent and at a temperature between 50° and 130° C. At the end of the reaction, the mixture is taken up in water to dissolve the amine salts formed, and the mixture is extracted with an appropriate solvent such as, for example, ethyl acetate. The resultant extract is then initially washed with an aqueous alkaline solution (NaOH or KOH) and then with water. The organic phase is then dried and the di-tertiary diamine is isolated either by distillation, or by concentration under reduced pressure.

Method 3

A primary amine of the formula RNH$_2$ is reacted with an arylsulfonyl halide, as indicated in Method 2. The resulting sulfonamide of the formula Ar—SO$_2$—NHR is then reacted with a dihalide of the formula Hal—A$_1$—Hal, at a temperature between about 80° and 140° C. The resulting disulfonamide, of the formula

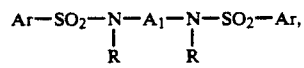

can be directly submitted, without being isolated, to acid hydrolysis. This acid hydrolysis can, for example, be carried out in an 85% aqueous solution of sulfuric acid, at a temperature between about 120° and 145° C., for a period of about 7 to 20 hours. The resulting di-secondary diamine, of the formula

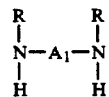

is then submitted to an alkylation reaction, in accordance with known procedures to form a di-tertiary diamine of the formula

Method 3 is particularly useful in the case where $A_1=(CH_2)_5$, for it avoids parasitic cyclization reaction observed with Methods 1 and 2 in this case.

Method 4

A secondary amine of the formula

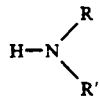

is reacted with a dihalide of the formula $Hal-A_1-Hal$, Hal and $A_1$ having the meanings given above, in the presence of an alkaline carbonate or a tertiary amine such as N-ethyl diisopropylamine.

When the reaction is carried out in the presence of an alkaline carbonate at least one mole of carbonate per mole of dihalide is employed. Ethanol is generally used as the solvent. At the end of the reaction, the mineral salts formed are filtered; the ethanol is expelled under reduced pressure; and the reaction products are separated by distillation.

When the reaction is carried out in the presence of a tertiary amine, at least two moles of secondary amine and tertiary amine per mole of dihalide are employed. The reaction is carried out, preferably, in the absence of a solvent and at a temperature between 50° and 130° C. At the end of the reaction, the mixture is taken up in water to dissolve the amine salts formed and the resulting mixture is extracted with an appropriate solvent such as, for example, ethyl acetate. The extract is washed initially with an aqueous alkaline solution, NaOH or KOH, and then with water. The organic phase is then dried and the di-tertiary diamine is isolated either by distillation, or by concentration under reduced pressure.

The secondary amine initial reactants wherein $R'=-CH_2-CH_2-OH$, are prepared by reacting a halogenated derivative of the formula R-Hal with monoethanol amine.

The secondary amine initial reactants, wherein R is other than $-CH_2-CH_2OH$, are obtained, for example, by reacting a primary amine of the formula $R-NH_2$ with an arylsulfonyl halide of the formula $Ar-SO_2-Hal$, Ar being an aryl group, for example phenyl or tolyl, and Hal being a halogen atom, for example a chlorine atom. A sulfonamide of the formula $Ar-SO_2-NHR$ is thus obtained which is then submitted to an alkylation reaction in accordance with known methods to form a sulfonamide of the formula

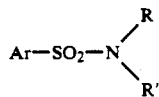

which, by acid hydrolysis, which includes the use of an aqueous solution of sulfuric acid, leads to a secondary amine of the formula

Method 5—applicable in the case where $A_1$ represents $-CH_2-CHOH-CH_2-$

Epichlorohydrin is reacted with a secondary amine of the formula $R-NH-R'$, employed preferably in excess. The reaction is carried out in solution or in suspension, in water, at a temperature between 40° and 100° C., with 3 to 10 moles of secondary amine per mole of epichlorohydrin being employed. After treatment of the reaction mixture with a basic solution, for example, a solution of NaOH or KOH, and extraction with an appropriate solvent, for example, ethyl acetate, a mixture of initial secondary amine and di-tertiary diamine is recovered and then separated by distillation.

Method 6—applicable in the case where $A_1$ represents $-(CH_2)_n-S-S-(CH_2)_n-$ An alkaline thiosulfate is reacted with an amine of the formula

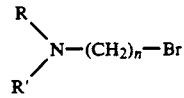

to form a Bunte salt that is hydrolyzed into the disulfide by means of an alkaline solution of NaOH or KOH. The reaction is carried out in water at a temperature between 40° and 100° C. As soon as the Bunte salt is completely formed, the corresponding disulfide is hydrolyzed and extracted in an appropriate solvent such as ethyl acetate. One eliminates the solvent by distillation under reduced pressure and isolates the di-tertiary diamine which can be purified, if desired, by distillation under reduced pressure.

The tertiary ω-halogenated amine used as an initial reactant in Process 2 described above can be prepared by utilizing the processes, described by M. R. Lehman, C. D. Thompson and C. S. Marvel, J.A.C.S. 55, 1977 (1933) and by Littman and Marvel, J.A.C.S. 52, 287, (1930), by replacing the dimethylamine initial reactant with an appropriate secondary amine of the formula

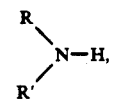

with R and R' being defined above. They can also be obtained by the reaction, in the presence of a proton acceptor, such as N-ethyl diisopropylamine, of a compound of the formula $Br-A-OC_6H_5$ with a secondary amine of the formula

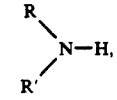

wherein A, R and R' have the meanings given above, followed by treatment of the resulting compound of the formula

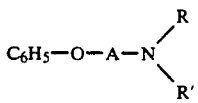

with H Br under the conditions described in the two J.A.C.S. references noted above.

Although the invention is not limited to the use of polymers I with any specified degree of polymerization, it will be noted that the polymers of formula I preferably employed in the present invention have a molecular weight ranging generally between 5,000 and 50,000. These polymers are generally soluble in at least one of the following three solvents: water, ethanol or a water-ethanol mixture. By evaporation of such a solvent from a solution of the polymer it is possible to obtain films which exhibit a good affinity for hair.

As indicated above, the polymers of formula I exhibit interesting cosmetic characteristics which permit their use in the preparation of cosmetic compositions.

Thus, the present invention also relates to a cosmetic composition characterized by the fact that it includes at least one polymer of formula I. Such cosmetic compositions include generally at least one adjuvant conventionally employed in cosmetic compositions.

The cosmetic compositions of the present invention include the polymers of formula I either as the principal active component or as an additive.

These cosmetic compositions can be provided in the form of aqueous, alcoholic or hydroalcoholic solutions, the alcohol being principally a lower alkanol such as ethanol or isopropanol, or in the form of a cream, gel, emulsion, or even in the form of an aerosol packaged under pressure in an aerosol container together with an aerosol propellant.

The adjuvants generally provided in the cosmetic compositions of the present invention are, for example, perfumes, dyes, preservatives, sequesterants, thickening agents and the like.

It is pointed out that the cosmetic compositions of the present invention can be ready-to-use compositions as well as concentrated compositions that are diluted before use. Thus, the cosmetic compositions of the invention are then not limited to any particular maximum concentration of the polymer of formula I contained therein.

In the cosmetic compositions of the present invention, the concentration of the polymers of formula I is at least 0.25% by weight. Generally, said concentration is between 0.5 and 10, preferably between 0.5 and 5, percent by weight The polymers of formula I exhibit principally interesting cosmetic properties when they are applied to the hair.

Thus, the present invention also relates to a process for treating hair which comprises applying to the hair the cosmetic composition defined above and containing at least one polymer of formula I, said composition being applied in an amount sufficient to provide a protective effect for the hair and/or to improve the quality of the hair.

When such a composition is applied to the hair, which composition can also contain other active substances for use in such treatments as a shampooing, dyeing, hair setting or the like, the composition significantly improves the quality of the hair and/or provides a protective effect for the hair.

For example, the composition of this invention provides protection to the hair by assisting and facilitating the untangling of wet or dry hair. Further, even when present in high concentrations in the cosmetic composition, the polymers of formula I do not impart a sticky feeling to the hair, wet or dry.

Moreover, unlike conventional cationic agents, the polymers of formula I do not render dry hair heavy. Thus, they facilitate the creation of bouffant hair styles and impart to dry hair such qualities as liveliness and a shiny appearance.

Moreover, polymers of formula I contribute effectively to the elimination of the drawbacks of hair sensitized by such treatments as bleaching, permanent waving or dyeing. It is known, for instance, that sensitized hair is often dry, dull and rough, and difficult to untangle and style and the use of polymers of formula I in compositions for sensitized hair overcomes such drawbacks.

Thus said polymers have a protective effect on hair, particularly on degraded hair.

Further, polymers of formula I exhibit, in particular, a great interest when they are employed as pretreating agents, principally before an anionic and/or nonionic shampoo, or before an oxidation dyeing, itself followed by an anionic and/or nonionic shampoo. The hair is then particularly easy to untangle and has a very soft feel.

Thus said polymers have also a protective effect on hair when applied before a cosmetic treatment, particularly before treatments having a degrading effect on hair.

These polymers are also useful as pretreating agents for other hair treatment operations, such as a permanent waving operation.

The cosmetic compositions according to the invention are principally cosmetic compositions for the hair, characterized by the fact that they include at least one polymer of formula I.

These cosmetic compositions for the hair include, generally, at least one adjuvant conventionally employed in cosmetic compositions for the hair.

These cosmetic compositions for the hair can be provided in the form of an aqueous, alcoholic or hydroalcoholic solution, the alcohol being a lower alkanol such as ethanol or isopropanol, or in the form of a cream, gel, emulsion or even in the form of a spray. They can also be packaged in the form of an aerosol under pressure in an aerosol container together with an aerosol propellant such as nitrogen, nitrous oxide or a Freon-type chlorofluorinated hydrocarbon.

The adjuvants generally provided in the cosmetic compositions for the hair in accordance with the present invention are for example, perfumes, dyes, preservatives, sequesterants, thickening agents, emulsifiers and the like, or even cosmetic resins conventionally employed in cosmetic compositions for the hair.

The polymers of formula I can be provided, in accordance with the present invention, either as an additive or as the principal active component in such cosmetic compositions as hair setting lotions, hair treating lotions, styling creams or gels. They can also be employed as an additive in shampoo compositions, hair setting compositions, permanent waving compositions, hair dye compositions, hair restructuring lotion compositions, anti-dandruff treating lotion compositions or hair lacquer compositions.

The cosmetic compositions for the hair according to the invention include then principally:

(a) hair treating compositions characterized in that they include, as the active component, at least one polymer of formula I in an aqueous or hydroalcoholic solution. The amount of polymer of formula I in such compositions can range between 0.25 and 10 percent by weight and, preferably, between 0.5 and 5 percent by weight of said composition.

The pH of these treating compositions is close to neutral and can range, for example, from 6 to 8. If necessary, the pH of such compositions can be adjusted to the value desired, by adding either and acid, such as citric acid, or a base, principally an alkanolamine such as monoethanolamine or triethanolamine.

To treat the hair with such a composition, the said composition is applied to wet hair and is permitted to remain in contact therewith for about 3 to 15 minutes. Thereafter, the hair is rinsed. If desired, the thus treated hair can then be subjected to a conventional hair setting operation;

(b) shampoo compositions characterized by the fact that they include at least one polymer of formula I and a cationic, nonionic or anionic detergent.

Representative cationic detergents usefully employed include, principally, long chain quaternary ammoniums, esters of fatty acids and amino alcohols or polyether amines.

Representative nonionic detergents are principally esters of polyols and sugars, polyethers of polyhydrogenated fatty alcohol and condensation products of ethylene oxide on fatty bodies or on long chain alkyl phenols or on long chain mercaptans or on long chain amides.

Representative anionic detergents are, principally, the alkaline salts, the ammonium salts or the amine or amino-alcohol salts of fatty acids, such as oleic acid, ricinoleic acid, copra oil acids or hydrogenated copra oil acids; the alkaline salts, the ammonium salts or the amino alcohol salts of the sulfates of fatty alcohols, principally fatty $C_{12}$–$C_{14}$ and $C_{16}$ alcohols; the alkaline salts, the magnesium salts, the ammonium salts or the amino alcohol salts of the sulfates of oxyethylenated fatty alcohols; the condensation products of fatty acids with isethionates, or with taurine, or with methyltaurine or with sarcosine and the like; alkylbenzene sulfonates, principally those wherein the alkyl moiety has 12 carbon atoms; alkylarylpolyether sulfates; monoglyceride sulfates and the like. All these anionic detergents, as well as numerous others not cited here, but which can be employed in the present invention, are well known and described in the literature.

These shampoo compositions can also contain various adjuvants such as, for example, perfumes, dyes, preservatives, thickening agents, foam stabilizers, softening agents or even one or more cosmetic resins.

In these shampoo compositions, the concentration of the detergent generally ranges between 5 and 50 weight percent and the concentration of the polymer of formula I generally ranges between 0.5 and 10 weight percent and preferably between 0.5 and 5 weight percent;

(c) hair setting lotions, principally, for sensitized hair, characterized by the fact that they contain at least one polymer of formula I, in an aqueous, alcoholic or hydroalcoholic solution.

Such hair setting lotions can also contain another cosmetic resin. The cosmetic resins useful in such lotions can be quite varied. They are principally vinylic or crotonic homopolymers or copolymers as, for example, polyvinyl pyrrolidone, copolymers of vinyl pyrrolidone and vinyl acetate, copolymers of crotonic acid and vinyl acetate and the like.

The concentration of the polymer of formula I in these hair setting lotion compositions can range generally between 0.25 and 10 weight percent and preferably between 0.5 and 3 weight percent. The other cosmetic resin can be present in essentially the same proportions.

The pH of these hair setting lotion compositions ranges generally between 3 and 9 and preferably between 4.5 and 7.5. The pH can be adjusted, if desired, by the addition, for example, of an alkanolamine such as monoethanolamine or triethanolamine;

(d) hair dye compositions characterized by the fact that they include at least one polymer of formula I, a dye and a carrier. Preferably, the carrier is selected so that the composition is a cream.

The concentration of the polymers of formula I in such hair dye compositions can range between 0.5–10 weight percent and preferably between 0.5 and 5 weight percent.

When the dye composition contains an oxidation dye, the dye composition can be packaged in two parts, one part containing both the oxidation dye and the polymer of formula I and the other part containing the oxidizing agent such as hydrogen peroxide. The two parts are mixed at the moment of use;

(e) hair lacquer compositions characterized by the fact that they include an alcoholic or hydroalcoholic solution of a conventional hair lacquer cosmetic resin and at least one polymer of formula I, this composition being packaged in an aerosol container, under pressure, together with an aerosol propellant.

A typical aerosol hair lacquer composition in accordance with the present invention can be provided by adding a conventional cosmetic resin and the polymer of formula I to a mixture of an anhydrous aliphatic alcohol, such as ethanol or isopropanol, and a propellant or a mixture of liquified propellants such as halogenated hydrocarbons including trichlorofluoromethane, dichloro difluoromethane and mixtures thereof.

In these hair lacquer compositions, the concentration of the cosmetic resin ranges generally between 0.5 and 3 weight percent, and the concentration of the polymer of formula I ranges generally between 0.25 and 10 weight percent.

However, it is possible to add to these hair lacquer compositions, in accordance with the invention, such adjuvants as dyes, plasticizers or any other conventional adjuvant;

(f) hair restructuring lotion compositions characterized by the fact that they include at least one agent having hair restructuring characteristics and at least one polymer of formula I.

The restructuring agents usefully employed in such lotions are, for example, methylol derivatives described in French patents 1,519,979; 1,159,980; 1,519,981; 1,519,982 and 1,527,085.

In these hair structuring lotions the concentration of the restructuring agent ranges generally between 0.1 and 10 weight percent and the concentration of the polymer of formula I ranges generally between 0.25 and 10 weight percent; and (g) pre-treatment compositions provided principally in the form of aqueous or hydroalcoholic solutions, optionally packaged in aerosol containers, or in the form of a cream or gel and capable of being applied to the hair before shampooing, principally before an anionic and/or nonionic shampooing and before oxidation dyeing followed by anionic and/or nonionic shampooing, or even before a permanent wave treatment.

In these pre-treatment compositions, the polymer of formula I constitutes the principal active component, and its concentration varies generally from 0.25 to 10 weight percent and preferably from 0.5 to 5 weight percent thereof. The pH of these compositions, approaching neutral, ranges generally between 3 and 9 and principally between 6 and 8.

These pre-treatment compositions can contain various adjuvants, for example, cosmetic resins conventionally employed in cosmetic compositions for the hair. They can also include pH modifiers, for example, amino alcohols such as monoethanolamine and triethanolamine.

The polymers of formula I also exhibit interesting cosmetic properties when they are applied to the skin.

Principally, they assist in the hydration of the skin and avoid then its drying out. They also impart to the skin a significant soft feeling.

The cosmetic compositions according to the invention can be cosmetic compositions for the skin characterized by the fact that they include at least one polymer of formula I.

Moreover, these compositions can include generally at least one adjuvant conventionally employed in cosmetic compositions for the skin and can be provided in the form of creams, gels, emulsions or aqueous, alcoholic or hydroalcoholic solutions.

The concentration of the polymer of formula I in these compositions for the skin ranges generally between 0.25 or and 10 weight percent.

The adjuvants generally employed in these cosmetic compositions are, for example, perfumes, dyes, preservatives, thickening agents, sequesterants, emulsifiers and the like.

These compositions for the skin constitute principally treating creams or lotions for the hands or face, anti-solar creams, tinting creams, make-up remover milks, bubble bath formulations or even deodorant compositions and can be prepared in accordance with conventional procedures.

For example, to obtain a cream, an aqueous phase containing in solution the polymer of formula I and optionally other components can be emulsified with an oil phase.

The oil phase can be made up of various materials such as paraffin oil, vaseline oil, sweet almond oil, avocado oil, olive oil, esters of fatty acids such as glyceryl monostearate, ethyl or isopropyl palmitate and alkyl myristates, such as the myristates of propyl, butyl or cetyl. Further, fatty alcohols such as cetyl alcohol or waxes such as, for example, beeswax can be added to such compositions.

The polymers of formula I can be provided, in accordance with the present invention, either as an additive, or as the principal active component, in such cosmetic compositions for the skin or treating creams or lotions for the hands or face, or as an additive in such compositions as anti-solar creams, tinting creams, make-up remover milks, bath oil formulations or bubble bath formulations and the like.

More particularly, the present invention relates to cosmetic compositions as defined above which include at least one of any one of the polymers described hereafter in Examples 1-140. These particular cosmetic compositions are either those for the hair or for the skin.

The present invention also relates to a process as defined above for a cosmetic treatment characterized by the fact that there is applied to the hair or to the skin at least one polymer of formula I in a cosmetic composition based on the polymer of formula I as defined above.

In particular, the present invention relates to a process for treating hair comprising applying to the hair, before an anionic shampoo or before an oxidation dyeing followed by an anionic shampooing, a pre-treatment composition containing at least one polymer of formula I as defined above.

The following non-limiting examples illustrate the present invention.

EXAMPLES OF PREPARING INITIAL REACTANT DIAMINES

Preparation No. 1—N,N'-dibutyl-N,N'-dimethyl diamino 1,6-hexane (a) 61 g of 1-dibromo hexane are slowly added, with agitation, to 91 g of n-butylamine previously heated to 75° C. At the end of the addition, the hydrobromide formed crystallizes and the temperature rises to 110° C. The reaction mixture is then cooled to 60° C. and there are introduced, successively, 250 cc of water and 50 cc of a concentrated aqueous solution of NaOH.

The agitation of the reaction mixture is continued for ½ hour. Thereafter, the precipitate, which is 1,6-N,N'-dibutyl diamino hexane, is separated from the reaction mixture by filtration and dried.

(b) 37 g of this latter product are added, with agitation and while maintaining the temperature lower than +5° C., to a mixture of 108 g of pure formic acid and 11 g of water. There are then introduced over a 10 minute period, 117 g of a 30% aqueous solution of formaldehyde. The temperature is then brought slowly to 100° C. The resulting mixture is agitated at this temperature until the end of the evolution of $CO_2$. The reaction mixture is then concentrated under reduced pressure and the residue made alkaline by the addition of about 150 cc of a concentrated aqueous solution of NaOH. This mixture is then extracted three times with 200 cc of isopropyl ether. The combined organic phases are worked three times with 100 cc of water, dried and concentrated. The residue is then distilled under vacuum and 72 g of 1,6-N,N'-dibutyl-N,N'-dimethyl diamino hexane, distilling at 98°-99° C., under 0.1 mm Hg are recovered.

Preparation No. 2—1,3-N,N'-dimethyl-N,N'-dioctyl diamino propane (a) N-methyl octylamine.

523 g of the benzene sulfonamide of octylamine are dissolved in 1500 cc of anhydrous xylene. There are then introduced, with agitation, 835 cc of a 2.4N ethanolic solution of sodium ethylate. The ethanol is then eliminated by distillation. While agitating the reaction mixture and maintaining its temperature at 100°-110° C., there are introduced over a one hour period 385 cc of methyl sulfate. The resulting mixture is heated at reflux for 4 hours. After cooling, the mineral salts formed are removed by filtration. There are then added to the filtrate 1500 cc of a concentrated aqueous solution of NaOH. The resulting mixture is decanted and the xylenic phase is washed 4 times with 1000 cc of water and then concentrated. The residue obtained is added to a mixture of 1400 g of concentrated sulfuric acid and about 560 g of crushed ice. The resulting mixture is then brought, with agitation, to 160° C. for 16 hours. After cooling, the reaction mixture is poured onto 3 kg of crushed ice and made alkaline by the addition of 3500 cc of a concentrated aqueous solution of NaOH, which is then extracted three times with 2000 cc of ethyl acetate. The organic phase is then washed with water, dried and concentrated under reduced pressure. The residue is distilled and the fraction distilling at 45°–50° C. under 0.2 mm Hg is recovered.

(b) 1,3-N,N'-dimethyl-N,N'-dioctyl diamino propane.

69 g of 1,3-dibromo propane are added to a mixture of 107 g of N-methyl octylamine and 87.5 g of N-ethyl-diisopropyl amine while maintaining the temperature at 100°–150° C. The resulting mixture is agitated for 7 hours at 120° C., and then cooled. To the cooled mixture there are added 500 cc of water and 200 cc of ether. The aqueous phase is decanted and the ether phase, treated with 50 cc of a concentrated aqueous solution of NaOH, is then decanted and washed three times with 100 cc of water. After drying, the ether is evaporated and then the unreacted N-methyl octylamine reactant is evaporated. The residue obtained includes two phases which are separated.

The upper clear phase is purified by distillation and the 1,3-N,N'-dimethyl-N,N'-dioctyl diamino propane distilling at 150°–153° C. under 0.5 mm Hg is recovered.

Preparation No. 3—1,5-N,N'-didecyl-N,N'-dimethyl diamino pentane (a) 1,5-N,N'-didecyl diamino pentane.

297 g of the benzene sulfonamide of N-decylamine are reacted with sodium ethylate, in a manner analogous to that described in Preparation No. 2, to form the corresponding sodium-containing derivative. After having eliminated the ethanol by evaporation, there are introduced, with agitation and at a temperature near 120° C., 162 g of 1,5-diiodopentane. The resulting mixture is heated for 4 hours at reflux of the xylene and then cooled. To the cooled mixture there are added with agitation, 500 cc of water to dissolve the mineral salts formed.

The organic phase is then decanted, dried and concentrated under reduced pressure. The residue obtained is heated for 14 hours at 130° C. in the presence of 300 cc of 85% sulfuric acid. After cooling, the reaction mixture is poured onto 1.5 kg of crushed ice. The pH is brought to 10 by the addition of a 30% aqueous solution of NaOH. The precipitate formed is separated by filtration, washed with water and dried. 1,5-N,N'-didecyl diamino pentane is thus obtained.

(b) 1,5-N,N'-didecyl-N,N'-dimethyl diamino pentane.

By methylating the product obtained in paragraph (a) above, in accordance with a method analogous to that described in Preparation No. 1, 1,5-N,N'-didecyl-N,N'-dimethyl pentane, B.P.=193°–195° C. (0.4 mm Hg), is obtained.

Preparation No. 4—1,3-N,N'-didodecyl-N,N'-dimethyl diamino propanol-2

26.6 g of epichlorohydrin are slowly added to a vigorously agitated mixture of 370 g of N-methyl dodecylamine and 600 cc of water. At the end of the addition, the reaction mixture is heated to 90° C. for 12 hours. After cooling, 10 cc of a concentrated aqueous solution of NaOH are added and the resulting mixture is extracted three times with 200 cc of ethyl acetate. The extraction solutions are dried on sodium sulfate and concentrated under reduced pressure. A first fraction corresponding to the excess N-methyl dodecylamine is thus obtained. A second fraction, distilling at 235°–240° C. under 1.5 mm Hg which is the desired di-tertiary diamine is recovered.

Preparation No. 5—1,3-N,N'-di(2-hydroxy)ethyl-N,N'-dioctyl diamino propane.

There is heated at reflux for 50 hours the following mixture:

100 g of N-(2-hydroxy)ethyl octylamine,
28.6 g of 1,3-dibromo propane,
22 g of potassium carbonate, and
300 cc of ethanol.

The mineral salts formed are removed by filtration; the ethanol is distilled off under reduced pressure; and then the residue is distilled under vacuum. The expected diamine distills at 200°–206° C. under 1 mm Hg.

Preparation No. 6

44 g of N-butyl-N-methyl 2-bromo ethylamine are dissolved in 10 cc of water. Then, while maintaining the temperature in the neighborhood of 0° C., the pH of the solution is adjusted to 7 by the addition of dilute NaOH. Then the temperature of the solution is raised to 60° C. while introducing a solution of 43.7 g of sodium thiosulfate (in the form of its pentahydrate) in 15.6 cc of water.

The resulting reaction mixture is maintained at 60° C. for 8 hours. Then after cooling, 71 cc of a concentrated aqueous solution of NaOH are added thereto. The reaction mixture is then left to stand for 2 hours, after which the organic phase is extracted with 100 cc of ethyl acetate. The extract is dried and concentrated under reduced pressure.

By distillation of the residue the expected diamine, BP=140°–150° C. (1.2 mm Hg), is obtained.

In an analogous manner, there have been prepared, in accordance with the methods described above, the di-tertiary diamines indicated in Table I below. These di-tertiary diamines are employed as initial reactants in the examples illustrating the preparation of polymers of formula I given hereafter.

TABLE I

| Preparation No. | Method No. | $A_1$ | R | R' |
|---|---|---|---|---|
| 7 | 2 | $(CH_2)_{10}$ | $CH_3$ | $C_{12}H_{25}$ |
| 8 | 1 | $(CH_2)_3$ | $CH_3$ | $C_4H_9$ |
| 9 | 2 | $(CH_2)_6$ | $CH_3$ | $C_8H_{17}$ |
| 10 | 2 | $(CH_2)_{10}$ | $CH_3$ | $C_8H_{17}$ |
| 11 | 1 | $(CH_2)_{10}$ | $CH_3$ | $C_4H_9$ |
| 12 | 2 | $(CH_2)_6$ | $CH_3$ | $C_{16}H_{33}$ |
| 13 | 1 | $(CH_2)_6$ | $CH_3$ | cyclohexyl |

TABLE I-continued

| Preparation No. | Method No. | A₁ | R | R' |
|---|---|---|---|---|
| 14 | 1 | $(CH_2)_6$ | $CH_3$ | isobutyl |
| 15 | 2 | $(CH_2)_3$ | $CH_3$ | $C_{12}H_{25}$ |
| 16 | 2 | $(CH_2)_6$ | $CH_3$ | $C_{12}H_{25}$ |
| 17 | 1 | p-xylylidene | $CH_3$ | $C_4H_9$ |
| 18 | 1 | m-xylylidene | $CH_3$ | $C_4H_9$ |
| 19 | 1 | $(CH_2)_{12}$ | $CH_3$ | $C_4H_9$ |
| 20 | 1 | $(CH_2)_6$ | $CH_3$ | $C_3H_7$ |
| 21 | 1 | $(CH_2)_6$ | $CH_3$ | isopropyl |
| 22 | 1 | $(CH_2)_3$ | $CH_3$ | benzyl |
| 23 | 1 | $-(CH_2)-CH-$ <br> $\quad\quad\quad\quad\;\; \mid$ <br> $\quad\quad\quad\quad\; CH_3$ | $CH_3$ | $C_6H_{13}$ |
| 24 | 1 | $(CH_2)_8$ | $CH_3$ | isobutyl |
| 25 | 1 | $\quad C_4H_9 \quad\quad C_4H_9$ <br> $\quad\quad \mid \quad\quad\quad\quad \mid$ <br> $HC-(CH_2)_5-CH$ <br> $\;\; \mid \quad\quad\quad\quad\quad \mid$ <br> $-CH_2 \quad\quad\; CH_2-$ | $CH_3$ | $C_8H_{17}$ |
| 26 | 1 | $-CH_2-CH-CH_2-$ <br> $\quad\quad\quad\quad\; \mid$ <br> $\quad\quad\quad\; C_{12}H_{25}$ | $CH_3$ | $C_4H_9$ |
| 27 |  | $CH_2-CH-CH_2$ <br> $\quad\quad\quad\; \mid$ <br> $\quad\quad\; OH$ | $CH_3$ | $C_{10}H_{21}$ |
| 28 |  | $CH_2-CH-CH_2$ <br> $\quad\quad\quad\; \mid$ <br> $\quad\quad\; OH$ | $CH_3$ | $C_8H_{17}$ |
| 29 |  | $(CH_2)_3$ | $-CH_2CH_2OH$ | $C_{12}H_{25}$ |
| 30 |  | $(CH_2)_6$ | $-CH_2CH_2OH$ | $C_{12}H_{25}$ |
| 31 |  | $(CH_2)_6$ | $-CH_2CH_2OH$ | $C_4H_9$ |
| 32 |  | $(CH_2)_2-S-S-(CH_2)_2$ | $CH_3$ | $C_{12}H_{25}$ |
| 33 |  | $(CH_2)_2-S-S-(CH_2)_2$ | $CH_3$ | $C_8H_{17}$ |

EXAMPLES OF PREPARATION OF POLYMERS OF FORMULA I

In all the examples below, the polymers are isolated, except where indicated to the contrary, by concentrating the reaction mixture under reduced pressure and drying under vacuum (in the order of 0.1 mm Hg), in the presence of phosphoric anhydride. In Examples 1-73, the process employed is process 1a described above.

Example 1

Polymer of Formula I wherein $R=R'=CH_3$, $A=(CH_2)_6$, $B=(CH_2)_3$ and $X=Br$.

There is agitated for 170 hours, at ambient temperature, a solution of:

172.3 g of N,N,N',N'-tetramethyl hexamethylene diamine and 202 g of 1,3-dibromo propane in 650 cc of a 50:50 mixture of methanol-dimethylformamide.

On the addition of anhydrous acetone a white precipitate is obtained which is then filtered and dried.

The polymer recovered contains 35.4% Br.

Example 2

Polymer of Formula I wherein $R=R'=CH_3$, $A=B=(CH_2)_6$ and $X=Br$.

There is heated at reflux for 24 hours, with agitation, the following solution:

172.3 g of N,N,N',N'-tetramethyl hexamethylene diamine and 244 g of 1,6-dibromo hexane in 1600 cc of anhydrous methanol.

The polymer obtained contains 36.6% Br and is soluble in water.

Example 3

Polymer of Formula I wherein $R=R'=CH_3$, $A=(CH_2)_2$,

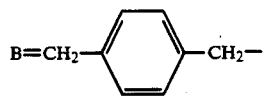

and $X=Br$.

There is heated at reflux for 50 hours the following mixture:

116.2 g of N,N,N',N'-tetramethyl ethylene diamine and 264 g of p-xylylidene bromide in 3200 cc of anhydrous methanol.

On cooling, a precipitate forms which is then filtered and dried. The resulting polymer contains 38.8% Br and is soluble in a water-ethanol mixture.

Example 4

Polymer of Formula I wherein $R=CH_3$, $R'=C_{12}H_{25}$, $A=(CH_2)_3$, $B=(CH_2)_6$ and $X=Br$.

There is heated at reflux for 80 hours the following solution:

438 g of N,N'-didodecyl-N,N'-dimethyl trimethylene diamine and 244 g of 1,6-dibromo hexane in 3200 cc of anhydrous methanol. The resulting polymer contains 23.4% Br and is soluble in ethanol.

Example 5

Polymer of Formula I wherein $R=CH_3$, $R'=C_4H_9$, $A=(CH_2)_6$, $B=(CH_2)_{10}$ and $X=Br$.

There is heated at reflux for 45 hours the following solution:

256 g of N,N'-dibutyl-N,N'-dimethyl hexamethylene diamine and 300 g of 1,10-dibromo decane in 3200 cc of anhydrous methanol. The resulting polymer contains 25.0% Br and is soluble in water and ethanol.

Example 6

Polymer of Formula I wherein $R=CH_3$, $R'=C_8H_{17}$, $A=(CH_2)_{10}$, $B=(CH_2)_4$ and $X=Br$.

There is heated at reflux for 60 hours the following solution:

424 g of N,N'-dimethyl-N,N'-dioctyl decamethylene diamine and 216 g of 1,4-dibromo butane in 3200 cc of anhydrous methanol. The resulting polymer contains 21.1% Br.

Example 7

Polymer of Formula I wherein $R=CH_3$, $R'=C_8H_{17}$, $A=(CH_2)_3$, $B=(CH_2)_4$ and $X=Br$.

There is heated at reflux for 60 hours the following solution:

326 g of N,N'-dimethyl-N,N'-dioctyl trimethylene diamine and 216 g of 1,4-dibromo butane.

The polymer obtained contains 26.0% Br.

Example 8

Polymer of Formula I wherein $R=CH_3$, $R'=C_{12}H_{25}$, $A=(CH_2)_{10}$, $B=(CH_2)_4$ and $X=Br$.

There is heated at reflux for 80 hours the following solution:

537 g of N,N'-didodecyl-N,N'-dimethyl decamethylene diamine and 216 g of 1,4-dibromo butane in 3200 cc of anhydrous methanol. The polymer obtained contains 20.6% Br and is soluble in ethanol.

Example 9

Polymer of Formula I wherein $R=R'=CH_3$, $A=B=(CH_2)_{10}$ and $X=Br$.

There is heated at reflux for 25 hours the following solution:

225 g of N,N,N',N'-tetramethyl decamethylene diamine and 301 g of 1,10-dibromo decane in 3200 cc of anhydrous methanol. The polymer obtained contains 28.0% Br.

Example 10

Polymer of Formula I wherein $R=CH_3$, $R'=C_8H_{17}$, $A=B=(CH_2)_6$ and $X=Br$.

There is heated at reflux for 40 hours the following solution:

368 g of N,N'-dimethyl-N,N'-dioctyl hexamethylene diamine and 244 g of 1,6-dibromo hexane in 3200 cc of anhydrous methanol. The polymer obtained contains 24.3% Br.

Example 11

Polymer of Formula I wherein $R=CH_3$, $R'=C_4H_9$, $A=(CH_2)_3$,

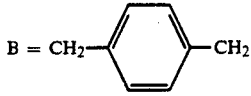

$B = CH_2-\phantom{x}-CH_2$ and $X=Br$.

There is heated at reflux for 65 hours the following mixture:

214 g of N,N'-dibutyl-N,N'-dimethyl trimethylene diamine and 264 g of p-xylylidene bromide in 1800 cc of methanol. The polymer obtained contains 30.7% Br and is soluble in water and in a water-ethanol mixture.

Example 12

Polymer of Formula I wherein $R=CH_3$, $R'=C_4H_9$, $A=B=(CH_2)_{10}$ and $X=Br$.

There is heated at reflux for 55 hours the following solution:

312 g of N,N'-dibutyl-N,N'-dimethyl decamethylene diamine and 301 g of 1,10-dibromo decane in 3200 cc of anhydrous methanol. The polymer obtained contains 32.9% Br and is soluble in water and in ethanol.

Example 13

Polymer of Formula I wherein $R=R'=CH_3$, $A=(CH_2)_6$, $B=(CH_2)_4$ and $X=Br$.

There is agitated for 170 hours, at ambient temperature, the following solution:

172.3 g of N,N,N',N'-tetramethyl hexamethylene diamine and 216 g of 1,4-dibromo butane in 650 cc of a 50:50 mixture of methanol and dimethylformamide. On addition thereto of anhydrous acetone, a white precipitate is obtained which is then filtered and dried. The polymer contains 36.6% Br and is soluble in water.

Example 14

Polymer of Formula I wherein $R=CH_3$, $R'=C_4H_9$, $A=(CH_2)_3$, $B=(CH_2)_4$ and $X=Br$.

There is heated at reflux for 70 hours, with agitation, the following solution:

214.4 g of N,N'-dibutyl-N,N'-dimethyl trimethylene diamine and 216 g of 1,4-dibromo butane in 3600 cc of anhydrous methanol. The polymer obtained contains 32.8% Br and is soluble in water and ethanol.

Example 15

Polymer of Formula I wherein $R=CH_3$, $R'=C_4H_9$, $A=B=(CH_2)_6$ and $X=Br$.

There is heated at reflux for 40 hours the following solution:

256 g of N,N'-dibutyl-N,N'-dimethyl hexamethylene diamine and 244 g of 1,6-dibromo hexane in 3600 cc of anhydrous methanol. The polymer contains 28.2% Br and is soluble in water and ethanol.

Example 16

Polymer of Formula I wherein R=CH₃, R'=C₁₂H₂₅, A=(CH₂)₆, B=(CH₂)₃ and X=Br.

There is heated at reflux for 30 hours the following solution:

480.9 g of N,N'-didodecyl-N,N'-dimethyl hexamethylene diamine and 202 g of 1,3-dibromo propane in a mixture of 2000 cc of aceonitrile and 4000 cc of isopropanol. The polymer formed contains 20.65% Br and is soluble in ethanol and a water-ethanol mixture.

Example 17

Polymer of Formula I wherein R=R'=CH₃, A=(CH₂)₃, B=(CH₂)₆ and X=Br.

There is heated at reflux for 55 hours the following solution:

130.2 g of N,N,N',N'-tetramethyl trimethylene diamine and 244 g of 1,6-dibromo hexane.

The polymer formed contains 39.6% Br and is soluble in water and ethanol.

Example 18

Polymer of Formula I wherein R=R'=CH₃, A=(CH₂)₂, B=(CH₂)₆ and X=Br.

There is heated at reflux for 50 hours the following solution:

116.2 g of N,N,N',N'-tetramethyl ethylene diamine and 244 g of 1,6-dibromo hexane in 3200 cc of anhydrous methanol. The polymer contains 41.9% Br and is soluble in water and in a water-ethanol mixture.

Example 19

Polymer of Formula I wherein R=R'=CH₃, A=(CH₂)₂, B=(CH₂)₁₀ and X=Br.

There is heated at reflux for 60 hours the following solution:

116.2 of N,N,N',N'-tetramethyl ethylene diamine and 300 g of 1,10-dibromo decane in 3200 cc of anhydrous methanol. The polymer obtained contains 34.1% Br and is soluble in ethanol and a water-ethanol mixture.

Example 20

Polymer of Formula I wherein R=R'=CH₃, A=(CH₂)₃,

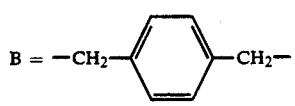

and X=Br.

There is heated at reflux for 70 hours the following mixture:

130.2 g of N,N,N',N'-tetramethyl trimethylene diamine and 264 g of p-xylylidene bromide in 3200 cc of anhydrous methanol. The polymer obtained contains 37.7% Br.

Example 21

Polymer of Formula I wherein R=R'=CH₃, A=(CH₂)₂, B=(CH₂)₄ and X=Br.

There is heated at reflux for 50 hours the following solution:

116.2 g of N,N,N',N'-tetramethyl ethylene diamine and 216 g of 1,4-dibromo butane in 3200 cc of anhydrous methanol. The polymer formed contains 45.8% Br and is soluble in water and in a water-ethanol mixture.

Example 22

Polymer of Formula I wherein R=R'=CH₃, A=(CH₂)₃, B=(CH₂)₄ and X=Br.

There is heated at reflux for 55 hours the following solution:

130.2 g of N,N,N',N'-tetramethyl trimethylene diamine and 216 g of 1,4-dibromo butane in 3200 cc of anhydrous methanol. The polymer formed contains 46.2% Br and is soluble in water and ethanol.

Example 23

Polymer of Formula I wherein R=R'=CH₃, A=(CH₂)₆,

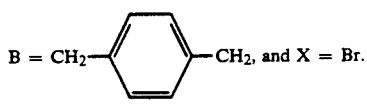

The following mixture is heated at reflux for 1 hour:

172.3 g of N,N,N',N'-tetramethyl hexamethylene diamine and 264 g of p-xylylidene bromide in 3200 cc of anhydrous methanol. After cooling the precipitate which has formed is filtered and dried. The polymer contains 34.6% Br and is soluble in water.

Example 24

Polymer of Formula I wherein R=R'=CH₃, A=(CH₂)₆, B=(CH₂)₁₀ and X=Br.

The following solution is heated at reflux for 15 hours:

172.3 g of N,N,N',N'-tetramethyl hexamethylene diamine and 300 g of 1,10-dibromo decane in 3200 cc of anhydrous methanol. The polymer obtained contains 32.7% Br and is soluble in water and ethanol.

Example 25

Polymer of Formula I wherein R=CH₃, R'=C₄H₉, A=(CH₂)₃, B=(CH₂)₁₀ and X=Br.

The following solution is heated at reflux for 70 hours:

214.4 g of N,N'-dibutyl-N,N'-dimethyl trimethylene diamine and 300 g of 1,10-dibromo decane in 3200 cc of anhydrous methanol. The polymer obtained contains 27.3% Br and is soluble in ethanol and in a water-ethanol mixture.

Example 26

Polymer of Formula I wherein R=R'=CH₃, A=(CH₂)₃, B=(CH₂)₁₀ and X=Br.

The following solution is heated at reflux for 38 hours:

130.2 g of N,N,N',N'-tetramethyl trimethylene diamine and 300 g of 1,10-dibromo decane in 3200 cc of anhydrous methanol. The polymer formed contains 34.3% Br and is soluble in water and in ethanol.

Example 27

Polymer of Formula I wherein $R=CH_3$, $R'=C_{12}H_{25}$, $A=(CH_2)_6$, $B=(CH_2)_4$ and $X=Br$.

The following solution is heated for 12 hours at 85° C.:

480.9 g of N,N'-didodecyl-N,N'-dimethyl hexamethylene diamine and 216 g of 1,4-dibromo butane in a mixture of 2000 cc of acetonitrile and 4000 cc of isopropanol. The polymer formed contains 20.4% Br and is soluble in ethanol.

Example 28

Polymer of Formula I wherein $R=CH_3$, $R'=C_{12}H_{25}$, $A=(CH_2)_6$, $B=(CH_2)_5$ and $X=Br$.

The following solution is heated for 28 hours at 85° C.:

480.9 g of N,N'-didodecyl-N,N'-dimethyl hexamethylene diamine and 230 g of 1,5-dibromo pentane in a mixture of 2000 cc of acetonitrile and 4000 cc of isopropanol. The polymer formed contains 19.9% Br and is soluble in ethanol.

By operating in accordance with methods analogous to those described in the preceding examples, there have been obtained, by Process 1 defined above, polymers of Formula I whose structure is indicated in Table II below.

TABLE II

| Ex. no | A | B | R | R' | X | Soluble in |
|---|---|---|---|---|---|---|
| 29 | $(CH_2)_6$ | $(CH_2)_5$ | $CH_3$ | $CH_3$ | Br | water |
| 30 | $(CH_2)_6$ | $(CH_2)_6$ | $CH_3$ | $C_{12}H_{25}$ | Br | ethanol water-ethanol |
| 31 | $(CH_2)_6$ | $(CH_2)_{10}$ | $CH_3$ | $C_{12}H_{25}$ | Br | ethanol water-ethanol |
| 32 | $(CH_2)_3$ | $(CH_2)_3$ | $CH_3$ | $C_{12}H_{25}$ | Br | ethanol |
| 33 | $(CH_2)_3$ | $(CH_2)_{10}$ | $CH_3$ | $C_{12}H_{25}$ | Br | ethanol |
| 34 | $(CH_2)_{10}$ | $(CH_2)_{10}$ | $CH_3$ | $C_{12}H_{25}$ | Br | ethanol |
| 35 | $(CH_2)_6$ | p-xylylidene | $CH_3$ | $C_{12}H_{25}$ | Br | ethanol |
| 36 | $(CH_2)_{10}$ | p-xylylidene | $CH_3$ | $C_{12}H_{25}$ | Br | ethanol |
| 37 | $(CH_2)_5$ | $(CH_2)_3$ | $CH_3$ | $C_{10}H_{21}$ | Br | ethanol water-ethanol |
| 38 | $(CH_2)_6$ | $(CH_2)_3$ | $CH_3$ | $C_{16}H_{33}$ | Br | ethanol |
| 39 | $(CH_2)_3$ | $(CH_2)_{10}$ | $CH_3$ | $C_8H_{17}$ | Br | ethanol |
| 40 | $(CH_2)_6$ | $(CH_2)_{10}$ | $CH_3$ | $C_8H_{17}$ | Br | ethanol |
| 41 | $(CH_2)_6$ | $(CH_2)_3$ | $CH_3$ | cyclohexyl | Br | water-ethanol, ethanol |
| 42 | $(CH_2)_6$ | $(CH_2)_3$ | $CH_3$ | iso-$C_4H_9$ | Br | water-ethanol, ethanol |
| 43 | $(CH_2)_6$ | Mixture [$(CH_2)_3$ 50 mole %, $(CH_2)_{10}$ 50 mole %] | $CH_3$ | $CH_3$ | Br | water, water-ethanol, ethanol |
| 44 | $(CH_2)_6$ | $(CH_2)_3$ | $CH_3$ | iso-$C_3H_7$ | Br | water, water-ethanol |
| 45 | $(CH_2)_3$ | $(CH_2)_6$ | $CH_3$ | benzyl | Br | ethanol, water-ethanol |
| 46 | $(CH_2)_6$ | $(CH_2)_3$ | $CH_3$ | $C_4H_9$ | Br | water, water-ethanol, ethanol |
| 47 | $(CH_2)_6$ + 1.6% by weight of terminal groups: $-N(C_2H_5)_3$ | $(CH_2)_3$ | $CH_3$ | $CH_3$ | Br | water, water-ethanol |
| 48 | $(CH_2)_6$ + 2.8% by weight of terminal groups: $-N(C_2H_5)_3$ | $(CH_2)_3$ | $CH_3$ | $CH_3$ | Br | water, water-ethanol |
| 49 | $(CH_2)_6$ + 7.4% by weight of terminal groups: $-N(C_2H_5)_3$ | $(CH_2)_3$ | $CH_3$ | $CH_3$ | Br | water, water-ethanol |
| 50 | $(CH_2)_6$ | $(CH_2)_4$ | $CH_3$ | $C_{10}H_{21}$ | Br | ethanol |
| 51 | $(CH_2)_6$ | p-xylylidene | $CH_3$ | $C_{10}H_{21}$ | Br | ethanol |
| 52 | p-xylylidene | $(CH_2)_3$ | $CH_3$ | $C_4H_9$ | Br | ethanol, water-ethanol |
| 53 | $(CH_2)_6$ | $(CH_2)_3$ | $-(CH_2)_2-O-(CH_2)_2-$ | | Br | water, water-ethanol |
| 54 | $(CH_2)_6$ | $(CH_2)_3$ | $CH_3$ | benzyl | Br | water, water-ethanol, ethanol |
| 55 | m-xylylidene | $(CH_2)_3$ | $CH_3$ | $C_4H_9$ | Br | water, water-ethanol, ethanol |
| 56 | $(CH_2)_8$ | $(CH_2)_3$ | $CH_3$ | iso-$C_4H_9$ | Br | water-ethanol, ethanol |
| 57 | $(CH_2)_6$ | $(CH_2)_3$ | $CH_3$ | $C_3H_7$ | Br | water, water-ethanol |
| 58 | $(CH_2)_{12}$ | $(CH_2)_3$ | $CH_3$ | $C_4H_9$ | Br | water, water-ethanol, ethanol |
| 59 | $(CH_2)_6$ | o-xylylidene | $CH_3$ | $C_8H_{17}$ | Br | ethanol |
| 60 | $(CH_2)_6$ | o-xylylidene | $CH_3$ | $CH_3$ | Br | water, water-ethanol |
| 61 | $(CH_2)_6$ | $(CH_2)_3$ | $CH_3$ | $CH_3$ | I | water, water-ethanol |
| 62 | $(CH_2)_{10}$ | $(CH_2)_3$ | $-(CH_2)_2-O-(CH_2)_2-$ | | Br | water, water-ethanol, ethanol |
| 63 | $(CH_2)_6$ | $-CH_2-CH_2-CH(CH_3)-$ | $CH_3$ | $CH_3$ | Br | water, water-ethanol, ethanol |

TABLE II-continued

| Ex. no | A | B | R | R' | X | Soluble in |
|---|---|---|---|---|---|---|
| 64 | $(CH_2)_{10}$ | $(CH_2)_4$ | $CH_3$ | $CH_3$ | Br | water, water-ethanol, ethanol |
| 65 | $(CH_2)_6$ | $-(CH_2)_3-CH$<br>\|<br>$CH_3$ | $CH_3$ | $CH_3$ | Br | water, water-ethanol, ethanol |
| 66 | $-CH_2-CH_2-CH-$<br>\|<br>$CH_3$ | $(CH_2)_6$ | $CH_3$ | $C_6H_{13}$ | Br | ethanol |
| 67 | $(CH_2)_3$ | $(CH_2)_6$ | \multicolumn{2}{c|}{$-(CH_2)-O-(CH_2)_2-$} | Br | water, water-ethanol |
| 68 | $(CH_2)_5$ | $(CH_2)_7$ | $CH_3$ | $CH_3$ | Br | water, water-ethanol, ethanol |
| 69 | $(CH_2)_5$ | $(CH_2)_9$ | $CH_3$ | $CH_3$ | Br | water, water-ethanol |
| 70 | $-CH_2-CH-(CH_2)_5-CH-CH_2-$<br>\|              \|<br>$C_4H_9$         $C_4H_9$ | $(CH_2)_3$ | $CH_3$ | $CH_3$ | Br | ethanol |
| 71 | $-CH_2-CH-(CH_2)_5-CH-CH_2-$<br>\|              \|<br>$C_4H_9$         $C_4H_9$ | $(CH_2)_6$ | $CH_3$ | $C_8H_{17}$ | Br | ethanol |
| 72 | $-CH_2-CH-CH_2-$<br>\|<br>$C_{12}H_{25}$ | $(CH_2)_3$ | $CH_3$ | $CH_3$ | Br | water-ethanol ethanol |
| 73 | $-CH_2-CH-CH_2-$<br>\|<br>$C_{12}H_{25}$ | $(CH_2)_6$ | $CH_3$ | $C_4H_9$ | Br | ethanol |

Example 74

Polymer of Formula I wherein $R=R'=CH_3$, $A=B=(CH_2)_{10}$ and $X=Br$.

50 g of 10-bromo decyl dimethylamine hydrobromide prepared in accordance with the disclosure of M. R. Lehman, C. D. Thompson and C. S. Marvel, J.A.C.S. 55, 1977 (1933) are dissolved in 200 cc of water. There is then added a 25% aqueous solution of NaOH until the pH thereof is 12. The mixture is then extracted with chloroform and the extract is evaporated to dryness. The resulting residue is dissolved in 250 cc of methanol and the resulting solution is heated at reflux for 24 hours.

On addition of ethyl acetate, a precipitate of the polymer formed is obtained which contains 27.8% Br.

The polymer is soluble in water and in ethanol and is practically identical to the product described in Example 9 above.

The 10-bromodecyl dimethylamine hydrobromide used as an initial reactant is obtained in the following manner: 12.6 g of 10-phenoxy decyl dimethylamine is dissolved in 63 cc of a 48% aqueous solution of HBr. The resulting solution is heated to 150° C. and distilled under atmospheric pressure until the temperature of the vapors reaches 125° C. There are then added 63 cc of 48% HBr and the distillation is resumed until 110 cc of distillate have been obtained. The residue is evaporated to dryness under reduced pressure and the hydrobromide obtained is purified by crystallization in an ethanolether mixture.

Example 75

Polymer of Formula I wherein $R=R'=CH_3$, $A=(CH_2)_6$, $B=CH_2$-$CHOH$-$CH_2$ and $X=Cl$.
Process 1a.

The following solution is heated at reflux for 50 hours:

172.3 g of N,N,N',N'-tetramethyl hexamethylene diamine,
129 g of 1,3-dichloro propanol-2 and
3200 cc of acetonitrile.

The polymer obtained contains 19.3% of Cl and is soluble in water and ethanol.

Example 76

Polymer of Formula I wherein $R=R'=CH_3$, $A=-(CH_2)_3-$, $B=-(CH_2)_2-O-(CH_2)_2-$ and $X=Cl$.
Process 1a.

The following mixture is heated, with agitation, at 100° C. for 32 hours:

130 g of N,N,N',N'-tetramethyl trimethyl diamine,
143 g of 2,2'-dichloro diethylether and
3200 cc of dimethyl formamide.

The precipitated polymer is filtered, washed with anhydrous acetone and dried. It contains 21.5% Cl and is soluble in water.

Example 77

Polymer of Formula I wherein $R'=CH_3$, $R=-CH_2-CH_2OH$, $A=(CH_2)_6$, $B=(CH_2)_3$ and $X=Br$.
Process 1a.

The following solution is heated at reflux for 170 hours:

232.3 g of N,N'-dihydroxyethyl-N,N'-dimethyl hexamethylene diamine,
202 g of 1,3-dibromo propane and
3200 cc of methanol.

The polymer obtained contains 31.5% Br and is soluble in water and in a 50:50 mixture of water and ethanol.

Example 78

Polymer of Formula I wherein R=R'=CH$_3$, A=-(CH$_2$)$_2$-S-S-(CH$_2$)$_2$-, B=(CH$_2$)$_5$ and X=Br.

Process 1a.

The following mixture is heated for 30 hours at 95° C., with agitation:

208.4 g of N,N-diemthyl 2-amino ethyl disulfide,
230 g of 1,5-dibromo pentane and 3200 cc of dimethyl formamide.

The polymer obtained contains 33.8% Br and is soluble in water and in a 50:50 water-ethanol mixture.

Example 79

Polymer of Formula I wherein R=R'=(CH$_2$)$_2$-O-(CH$_2$)$_2$, B=CH$_2$-CHOH-CH$_2$, A=(CH$_2$)$_6$ and X=Br.

Process 1b.

The following solution is heated at reflux for 300 hours:

230.3 g of 1,3-dimorpholino propanol-2,
244 g of 1,6-dibromo hexane and
3200 cc of methanol.

The polymer obtained contains 30.0% Br and is soluble in water and in a 50:50 mixture of water and ethanol.

Example 80

Polymer of Formula I wherein R=R'=CH$_3$,

A = —⟨C$_6$H$_4$⟩—CH$_2$—⟨C$_6$H$_4$⟩—,

B=(CH$_2$)$_3$ and X=Br.

Process 1a.

The following solution is heated at reflux for 26 hours:

254 g of 4,4'-N,N,N',N'-tetramethyl diamino diphenyl methane,
202 g of 1,3-dibromo propane,
900 cc of dimethyl formamide and
900 cc of methanol.

The methanol is evaporated and 2000 cc of anhydrous acetone are added thereto. The resulting mixture is cooled and the polymer formed is filtered therefrom. The polymer contains 25.8% Br and is soluble in water and in a 50:50 mixture of water and ethanol.

Example 81

Polymer of Formula I wherein R=R'=CH$_3$, A=-(CH$_2$)$_2$-O-(CH$_2$)$_2$-, B=-CH$_2$-C$_6$H$_4$-CH$_2$-(para) and X=Br.

Process 1a.

The following solution is heated at reflux for 60 hours:

160.3 g of 2,2'-bis(dimethylamino) diethyl ether,
264 g of p-xylylidene bromide,
1000 cc of acetonitrile and
4000 cc of isopropanol.

The polymer obtained contains 33.8% Br and is soluble in water and in a 50:50 mixture of water and ethanol.

In an analogous fashion, the quaternized polymers identified in Table III, below, have been prepared.

TABLE III

| Ex. n° | R | R' | A | B | X | Soluble in | Process |
|---|---|---|---|---|---|---|---|
| 82 | CH$_2$CH$_2$OH | CH$_3$ | (CH$_2$)$_3$ | (CH$_2$)$_6$ | Br | Water, water-ethanol | 1a |
| 83 | CH$_2$CH$_2$OH | CH$_3$ | (CH$_2$)$_3$ | (CH$_2$)$_{10}$ | Br | Water | 1a |
| 84 | CH$_2$CH$_2$OH | C$_8$H$_{17}$ | (CH$_2$)$_3$ | —CH$_2$—CHOH—CH$_2$— | Br | Ethanol, water-ethanol | 1a |
| 85 | CH$_2$CH$_2$OH | C$_8$H$_{17}$ | (CH$_2$)$_3$ | —CH$_2$-(p-C$_6$H$_4$)-CH$_2$— | Br | Ethanol | 1a |
| 86 | CH$_2$CH$_2$OH | C$_{12}$H$_{25}$ | (CH$_2$)$_6$ | (CH$_2$)$_3$ | Br | Ethanol | 1a |
| 87 | CH$_2$CH$_2$OH | CH$_3$ | (CH$_2$)$_{10}$ | (CH$_2$)$_3$ | Br | Ethanol, water-ethanol | 1a |
| 88 | CH$_2$CH$_2$OH | CH$_3$ | —CH$_2$-(m-C$_6$H$_4$)-CH$_2$— | (CH$_2$)$_6$ | Br | Ethanol, water-ethanol | 1a |
| 89 | CH$_2$CH$_2$OH | C$_4$H$_9$ | (CH$_2$)$_6$ | —(CH$_2$)$_2$—O—(CH$_2$)$_2$— | Br | Ethanol, water-ethanol | 1a |
| 90 | CH$_2$CH$_2$OH | CH$_3$ | (CH$_2$)$_3$ | —CH$_2$—CHOH—CH$_2$ | Br | Water, water-ethanol | 1b |
| 91 | CH$_3$ | CH$_3$ | —(CH$_2$)$_2$—S—S—(CH$_2$)$_2$— | (CH$_2$)$_3$ | Br | Water, water-ethanol | 1a |
| 92 | CH$_3$ | C$_8$H$_{17}$ | —(CH$_2$)$_2$—S—S—(CH$_2$)$_2$— | (CH$_2$)$_3$ | Br | Ethanol, water-ethanol | 1a |
| 93 | CH$_3$ | CH$_3$ | —(CH$_2$)$_2$—S—S—(CH$_2$)$_2$— | (CH$_2$)$_4$ | Br | Water, water-ethanol | 1* |
| 94 | CH$_3$ | CH$_3$ | —(CH$_2$)$_2$—S—S—(CH$_2$)$_2$— | (CH$_2$)$_6$ | Br | Water, water-ethanol | 1a |
| 95 | CH$_3$ | C$_{12}$H$_{25}$ | —(CH$_2$)$_2$—S—S—(CH$_2$)$_2$— | (CH$_2$)$_6$ | Br | Ethanol, water-ethanol | 1a |
| 96 | CH$_3$ | CH$_3$ | —(CH$_2$)$_2$—S—S—(CH$_2$)$_2$— | —CH$_2$—CHOH—CH$_2$— | Br | Water, water-ethanol | 1a |
| 97 | CH$_3$ | CH$_3$ | —(CH$_2$)$_2$—S—S—(CH$_2$)$_2$— | (CH$_2$)$_{10}$ | Br | Water, water-ethanol | 1a |
| 98 | CH$_3$ | CH$_3$ | —(CH$_2$)$_2$—S—S—(CH$_2$)$_2$— | —(CH$_2$)$_2$—O—(CH$_2$)$_2$ | Br | Water, water-ethanol | 1a |
| 99 | CH$_3$ | C$_4$H$_9$ | —(CH$_2$)$_2$—S—S—(CH$_2$)$_2$— | —CH$_2$-(m-C$_6$H$_4$)-CH$_2$— | Br | Water, water-ethanol | 1a |

TABLE III-continued

| Ex. n° | R | R' | A | B | X | Soluble in | Process |
|---|---|---|---|---|---|---|---|
| 100 | CH₃ | CH₃ | —(CH₂)₂—S—S—(CH₂)₂— | —CH₂—⟨C₆H₄⟩—CH₂— | Br | Water, water-ethanol | 1a |
| 101 | CH₃ | CH₃ | —(CH₂)₃—S—S—(CH₂)₃— | (CH₂)₃ | Br | Water, water-ethanol | 1a |
| 102 | CH₃ | CH₃ | —(CH₂)₂—O—(CH₂)₂— | —(CH₂)₂—O—(CH₂)₂— | Br | Water, water-ethanol | 1a |
| 103 | CH₃ | CH₃ | —(CH₂)₃—O—(CH₂)₃— | (CH₂)₃ | Br | Water, water-ethanol | 1a |
| 104 | CH₃ | CH₃ | —(CH₂)₃—O—(CH₂)₂— | —CH₂—CHOH—CH₂— | Br | Water, water-ethanol | 1b |
| 105 | CH₃ | CH₃ | (CH₂)₃ | —CH₂—CHOH—CH₂— | Br | Water, water-ethanol | 1b |
| 106 | CH₃ | CH₃ | (CH₂)₄ | —CH₂—CHOH—CH₂ | Br | Water | 1b |
| 107 | CH₃ | CH₃ | (CH₂)₅ | —CH₂—CHOH—CH₂ | Br | Water, water-ethanol | 1b |
| 108 | CH₃ | CH₃ | (CH₂)₆ | —CH₂—CHOH—CH₂— | Br | Water, water-ethanol | 1b |
| 109 | —(CH₂)₅— | | (CH₂)₆ | —CH₂—CHOH—CH₂— | Br | Water, ethanol | 1b |
| 110 | CH₃ | CH₃ | (CH₂)₁₀ | —CH₂—CHOH—CH₂ | Br | Water, ethanol | 1b |
| 111 | CH₃ | CH₃ | —CH₂—⟨C₆H₄⟩—CH₂— | —CH₂—CHOH—CH₂ | Br | Water, water-ethanol | 1b |
| 112 | CH₃ | CH₃ | —(CH₂)₂—S—(CH₂)₂— | (CH₂)₃ | Br | Water, water-ethanol | 1a |
| 113 | CH₃ | CH₃ | —(CH₂)₂—SO—(CH₂)₂— | (CH₂)₃ | Br | Water, water-ethanol | 1a |
| 114 | CH₃ | CH₃ | —(CH₂)₂—SO₂—(CH₂)₂— | (CH₂)₆ | Br | Water, water-ethanol | 1a |
| 115 | CH₃ | CH₃ | (CH₂)₆ | —CH₂—CHOH—CH₂— | Br | Water, water-ethanol | 1a |
| 116 | CH₃ | C₄H₉ | (CH₂)₁₀ | —CH₂—CHOH—CH₂— | Br | Water, ethanol | 1a |
| 117 | CH₃ | C₄H₉ | —CH₂—⟨C₆H₄⟩—CH₂— | —(CH₂)₂—O—(CH₂)₂— | Br | Water, water-ethanol | 1a |
| 118 | CH₃ | C₁₂H₂₅ | (CH₂)₃ | —(CH₂)₂—O—(CH₂)₂— | Br | Ethanol | 1a |
| 119 | CH₃ | CH₃ | (CH₂)₆ | —(CH₂)₂—O—(CH₂)₂— | Cl | Water, water-ethanol | 1a |
| 120 | CH₃ | C₈H₁₇ | (CH₂)₆ | —(CH₂)₂—O—(CH₂)₂— | Br | Ethanol, water-ethanol | 1a |
| 121 | CH₃ | CH₃ | (CH₂)₄ | (CH₂)₇ | Br | Water, ethanol | 1a |
| 122 | CH₃ | CH₃ | (CH₂)₄ | (CH₂)₉ | Br | Water, ethanol | 1a |
| 123 | CH₃ | CH₃ | (CH₂)₄ | o-⟨C₆H₄⟩(CH₂)(CH₂) | Br | Water | 1a |
| 124 | CH₃ | CH₃ | (CH₂)₅ | —(CH₂)₂—CH(CH₃)— | Br | Water, ethanol | 1a |
| 125 | CH₃ | CH₃ | (CH₂)₂—O—(CH₂)₂ | (CH₂)₃ | Br | Water | 1a |
| 126 | CH₃ | CH₃ | —⟨C₆H₄⟩—CH₂—⟨C₆H₄⟩— | —CH₂—CH(OH)—CH₂— | Br | Ethanol | 1a |
| 127 | CH₃ | CH₃ | —⟨C₆H₄⟩—CH₂—⟨C₆H₄⟩— | (CH₂)₂—O—(CH₂)₂ | Br | Water, ethanol | 1a |
| 128 | —(CH₂)₅— | | —(CH₂)₂—CH(CH₃)— | CH₂—CH(OH)—CH₂ | Br | Water | 1b |
| 129 | —(CH₂)₅— | | m-⟨C₆H₄⟩(CH₂)(CH₂) | CH₂—CH(OH)—CH₂ | Br | Water | 1b |
| 130 | CH₃ | isoC₃H₇ | (CH₂)₃ | (CH₂)₇ | Br | Water, ethanol | 1a |

TABLE III-continued

| Ex. n° | R | R' | A | B | X | Soluble in | Process |
|---|---|---|---|---|---|---|---|
| 131 | $CH_3$ | $isoC_3H_7$ | $(CH_2)_3$ | $(CH_2)_3$ | Br | Water | 1a |
| 132 | $CH_3$ | $C_3H_7$ | $(CH_2)_6$ | $-(CH_2)_3-CH(CH_3)-$ | Br | Water | 1a |
| 133 | $CH_3$ | $C_3H_7$ | $(CH_2)_6$ | o-xylylene ($-CH_2-C_6H_4-CH_2-$) | Br | ethanol | 1a |
| 134 | $CH_3$ | benzyl | $(CH_2)_3$ | $CH_2-CH(OH)-CH_2$ | Br | Water, ethanol | 1a |
| 135 | $CH_3$ | benzyl | $(CH_2)_6$ | $CH_2-CH(OH)-CH_2$ | Cl | Ethanol | 1a |
| 136 | $CH_3$ | $C_4H_9$ | m-xylylene ($-CH_2-C_6H_4-CH_2-$) | $CH_2-CH(OH)-CH_2$ | Br | Water | 1a |
| 137 | $CH_3$ | $CH_3$ | p-xylylene ($-CH_2-C_6H_4-CH_2-$) | $CH_2-CH(OH)-CH_2$ | Br | Water, ethanol | 1a |
| 138 | $CH_3$ | $C_3H_7$ | m-xylylene ($-CH_2-C_6H_4-CH_2-$) | $(CH_2)_{10}$ | Br | Water, ethanol | 1a |
| 139 | $CH_3$ | $C_3H_7$ | $(CH_2)_3$ | $(CH_2)_4$ | Br | Water, ethanol | 1a |
| 140 | $CH_3$ | $C_3H_7$ | $(CH_2)_6$ | $(CH_2)_4$ | Br | Water, ethanol | 1a |
| 141 | $CH_3$ | $CH_3$ | $(CH_2)_3$ | $(CH_2)_6$ | Cl | Water, ethanol | 1a |

EXAMPLES OF COSMETIC COMPOSITIONS AND TREATMENTS

Example I

Hand Treating Cream

1. The following cream is prepared:

| | |
|---|---|
| Vaseline oil | 10 g |
| Cetyl alcohol | 6 g |
| Glyceryl monostearate - self-emulsifying | 4 g |
| Triethanolamine | 2 g |
| Methyl p-hydroxy benzoate | 0.1 g |
| Polymer of Example 1 | 4 g |
| Water, q.s.p. | 100 g |

This cream is applied to the hands with rubbing so as to achieve good penetration. The hands are soft and have a pleasant feel.

2. Analogous results are obtained by replacing in the above hand cream composition, the 4 g of the polymer of Example 1 by 3.5 g of the polymer of Example 15.

Example II

Oxidation Hair Dye Cream Support

1. The following cream is prepared:

| | |
|---|---|
| Cetyl stearyl alcohol | 20 g |
| Oleic diethanolamide | 4 g |
| Sodium cetyl stearyl sulfate | 3 g |
| Polymer of Example 15 | 5 g |
| Ammonia, 22° Bé (11N) | 10 ml |
| M-diamino anisol sulfate | 0.048 g |
| Resorcin | 0.420 g |
| M-amino phenol base | 0.150 g |
| Nitro-p-phenylene diamine | 0.085 g |
| p-toluylene diamine | 0.004 g |
| Trilon B - tetrasodium salt ethylene diamine tetra-acetic acid | 1 g |
| Sodium bisulfite, d = 1.32 | 1.200 g |
| Water, q.s.p. | 100 g |

30 g of this cream are mixed with 45 g of $H_2O_2$ (20 volumes) thus producing a glossy, thick, pleasant to apply cream which adheres well to the hair. This cream is permitted to remain in contact with the hair for 30 minutes, after which the hair is rinsed and dried. When so applied to 100% white hair, a blond coloration is obtained and the hair, wet or dry, is easy to untangle and has a shiny appearance, and a pleasant and silky feel.

2. The following cream is prepared:

| | |
|---|---|
| Cetyl stearyl alcohol | 20 g |
| Oleic diethanolamide | 4 g |
| Sodium cetyl stearyl sulfate | 3 g |
| Polymer of Example 3 | 5 g |
| Ammonia, 22° Bé (11N) | 12 ml |
| M-diamino anisol sulfate | 0.048 g |
| Resorcin | 0.420 g |
| M-amino phenol base | 0.150 g |
| Nitro p-phenylene diamine | 0.085 g |
| P-toluylene diamine | 0.004 g |
| Trilon B | 1 g |
| Sodium bisulfite, d = 1.32 | 1.200 g |
| Water, q.s.p. | 100 g |

30 g of this cream are mixed with 45 g of H₂O₂ (20 volumes) thus producing a glossy, thick and pleasant to apply cream which adheres well to the hair. The cream is permitted to remain in contact with the hair for 30 minutes, after which the hair is rinsed and dried. When so applied to 100% white hair, a blond coloration is achieved. The hair, wet or dry, is easy to untangle and has a shiny appearance and a pleasant and silky feel.

Example III

Hair Setting Lotions for Sensitized Hair

1. An alcoholic lotion is prepared as follows:

| | |
|---|---|
| Polyvinylpyrrolidone (MW 40,000) | 1 g |
| Polymer of Example 7 | 1 g |
| Ethyl alcohol, q.s.p. | 100 ml |

The resulting lotion is applied to the hair which is then set in the desired style and dried. The hair is hard and plasticized, is shiny and has body, and has a silky feel and is easily untangled.

2. Analogous results are obtained by replacing in the above composition the polymer of Example 7 by the polymer of Example 16.

3. The following lotion is prepared:

| | |
|---|---|
| Polymer of Example 18 | 0.8 g |
| Copolymer of vinylpyrrolidone/ vinyl acetate, 60:40 K value (1% ethanol solution) = 25-35 | 1.0 g |
| Triethanolamine, q.s.p. | pH 6 |
| Water, q.s.p. | 100 ml |

The composition is applied to bleached hair which is then set and dried. The results achieved are analogous to those obtained in the preceding example.

4. The following lotion is prepared:

| | |
|---|---|
| Polymer of Example 19 | 1 g |
| Copolymer of vinylpyrrolidone/ vinyl acetate, 60/40 K value (1% ethanol solution) = 25-35 | 1 g |
| Ethyl alcohol, q.s.p. | 50° |
| Triethanolamine, q.s.p. | pH 7 |
| Water, q.s.p. | 100 ml |

The lotion is applied to bleached hair which is then set and dried. Results analogous to those achieved in the preceding example are obtained.

5. The following lotion is prepared:

| | |
|---|---|
| Polymer of Example 17 | 1.5 g |
| Copolymer of vinyl acetate/ crotonic acid, 90:10, MW = 20,000 | 1.5 g |
| Triethanolamine, q.s.p. | pH 7.5 |
| Water, q.s.p. | 100 ml |

This lotion is applied to bleached hair which is then set and dried. Results analogous to those achieved in the preceding example are obtained.

6. The following composition is prepared:

| | |
|---|---|
| Polymer of Example 2 | 1.59 |
| Copolymer of vinyl acetate/ crotonic acid, 90:10 MW = 20,000 | 1.59 |
| Monoethanolamine, q.s.p. | pH 7 |
| Water, q.s.p. | 100 ml |

This composition is applied to bleached hair which is then set and dried. Results analogous to those obtained in the preceding example are attained.

Example IV

Hair Treating Lotions—Application With Rinsing 1. 30 ml of the following lotion are applied to wet, clean hair:

| | |
|---|---|
| Polymer of Example 20 | 5 g |
| Monoethanolamine, q.s.p. | pH 7.5 |
| Water, q.s.p. | 100 ml |

This lotion is permitted to remain in contact with the hair for 5 minutes, after which the hair is rinsed. The hair has a soft feel and is easy to untangle. The hair is then set and dried. The dry hair untangles easily and is shiny and lively and has body.

2. 25 ml of the following lotion are applied to wet, clean hair:

| | |
|---|---|
| Polymer of Example 12 | 6 g |
| Citric acid, q.s.p. | pH 6 |
| Water, q.s.p. | 100 ml |

The lotion is permitted to remain in contact with the hair for 5 minutes, after which the hair is rinsed. The hair has a soft feel and is easy to untangle. The hair is then set and dried. The dry hair is easy to untangle, is shiny and lively and has body.

3. 25 ml of the following lotion are applied to wet, clean hair:

| | |
|---|---|
| Polymer of Example 21 | 6 g |
| Triethanolamine, q.s.p. | pH 6 |
| Water, q.s.p. | 100 ml |

This lotion is permitted to remain in contact with the hair for 5 minutes, after which the hair is rinsed. The hair has a soft feel and is easy to comb. The hair is then set and dried. The dry hair is easy to comb, is shiny and lively and has body.

4. 30 ml of the following lotion having a pH of about 7 are applied to wet, clean hair:

| | |
|---|---|
| Polymer of Example 22 | 7 g |

-continued

| Water, q.s.p. | 100 ml |

This lotion is permitted to remain in contact with the hair for 5 minutes, after which the hair is rinsed. The hair has a soft feel and is easy to comb. The hair is then set and dried. The dry hair is easy to comb, is shiny and lively and has body.

5. 25 ml of the following lotion are applied to wet, clean hair:

| Polymer of Example 23 | 5 g |
| Monoethanolamine, q.s.p. | pH 5 |
| Water, q.s.p. | 100 ml |

This lotion is permitted to remain in contact with the hair for 5 minutes, after which it is rinsed. The hair has a soft feel and is easy to untangle. The hair is then set and dried. The dry hair is easy to comb, is shiny and lively and has body.

Example V

Hair Restructuring Lotion—Application Without Rinsing

1. Before use of 0.3 g of N,N'-di-(hydroxymethyl) ethylene thiourea, hereinafter called compound A, is mixed with 25 ml of the following solution:

| Polymer of Example 11 | 0.6 g |
| HCl, q.s.p. | pH 2.7 |
| Water, q.s.p. | 100 ml |

This mixture is applied to washed and dried hair before setting the same. The hair combs easily and has a silky feel. The hair is then set and dried. The hair is shiny, lively and has body. It has a silky feel and combs easily.

2. Before use 0.4 g of compound A is mixed with 25 ml of the following solution:

| Polymer of Example 14 | 0.25 g |
| Phosphoric acid, q.s.p. | pH 2.7 |
| Water, q.s.p. | 100 ml |

This mixture is applied to washed and dried hair before being set. The hair combs easily and has a silky feel. The hair is then set and dried. The hair is shiny and lively, has body, has a silky feel and is easy to comb.

3. Before use, 0.5 g of compound A is mixed with 25 ml of the following solution:

| Polymer of Example 24 | 0.6 g |
| Phosphoric acid, q.s.p. | pH 3 |
| Water, q.s.p. | 100 ml |

This mixture is applied to washed and dried hair before being set. The hair combs easily and has a silky feel. The hair is set and dried. The hair is shiny and lively, has body, has a silky feel and combs easily.

4. Before use, 0.6 g of compound A is mixed with 25 ml of the following solution:

| Polymer of Example 13 | 0.7 g |
| HCl, q.s.p. | pH 3 |

-continued

| Water, q.s.p. | 100 ml |

This lotion is applied to washed and dried hair before being set. The hair is easily untangled and has a silky feel. The hair is then set and dried. The hair is shiny and lively, has body, has a silky feel and combs easily.

5. Before use, 0.5 g of compound A is mixed with 25 ml of the following solution:

| Polymer of Example 1 | 0.5 g |
| Phosphoric acid, q.s.p. | pH 3 |
| Water, q.s.p. | 100 ml |

This lotion is applied to washed and dried hair before being set. The hair is easy to untangle and has a silky feel. The hair is then set and dried. The hair is shiny and lively, has body, has a silky feel and combs easily.

Example VI

Hair Structuring Lotion—Application With Rinsing

1. Before use, 2 g of compound A are mixed with 25 ml of the following solution:

| Polymer of Example 25 | 5 g |
| HCl, q.s.p. | pH 2.5 |
| Water, q.s.p. | 100 ml |

This lotion is applied to washed and dried hair and is permitted to remain in contact therewith for 10 minutes, after which the hair is rinsed. The hair is easy to untangle and has a silky feel. The hair is then set and dried under a hood. The dry hair is easy to comb, is shiny and lively and has body.

2. Before use, 1.8 g of compound A are mixed with 25 ml of the following solution:

| Polymer of Example 26 | 6 g |
| Phosphoric acid, q.s.p. | pH 3 |
| Water, q.s.p. | 100 ml |

This lotion is applied to washed and dried hair and is permitted to remain in contact therewith for 10 minutes, after which the hair is rinsed. The hair is easy to untangle and has a silky feel. The hair is then set and dried under a hood. The dry hair combs easily, is shiny and lively and has body.

3. Before use, 1.5 g of compound A are mixed with 25 ml of the following solution:

| Polymer of Example 13 | 4 g |
| HCl, q.s.p. | pH 3 |
| Water, q.s.p. | 100 ml |

This lotion is applied to washed and dried hair and is permitted to remain in contact therewith for 10 minutes, after which the hair is rinsed. The hair is easy to untangle and has a silky feel. The hair is then set and dried under a hood. The dry hair combs easily, is shiny and lively and has body.

4. Before use, 2 g of compound A are mixed with 25 ml of the following solution:

| | |
|---|---|
| Polymer of Example 1 | 5 g |
| Phosphoric acid, q.s.p. | pH 2.8 |
| Water, q.s.p. | 100 ml |

This lotion is applied to washed and dried hair and is permitted to remain in contact therewith for 10 minutes, after which the hair is rinsed. The hair is easy to untangle and has a silky feel. The hair is then set and dried under a hood. The dry hair combs easily, is shiny and lively and has body.

5. Before use, 1.5 g of compound A are mixed with 25 ml of the following solution:

| | |
|---|---|
| Polymer of Example 11 | 5.5 g |
| Phosphoric acid, q.s.p. | pH 3 |
| Water, q.s.p. | 100 ml |

This lotion is applied to washed and dried hair and is permitted to remain in contact therewith for 10 minutes after which the hair is rinsed. The hair is easy to untangle and has a silky feel. The hair is then set and dried under a hood. The dry hair is easily combed, is shiny and lively and has body.

Example VII

Shampoo Compositions

1. The following shampoo composition is prepared:

| | |
|---|---|
| $C_{11}$–$C_{14}$ α-diol condensed with 3–4 moles of glycidol | 17 g |
| Polymer of Example 1 | 3 g |
| Lactic acid, q.s.p. | pH 3.5 |
| Water, q.s.p. | 100 cc |

When applied to the head, this clear solution produces a sufficiently mild and abundant foam and facilitates untangling wet hair. After rinsing and drying, the hair is lively, light and shiny.

2. The following shampoo composition is prepared:

| | |
|---|---|
| Lauryl ether condensed with 4 moles of glycerol | 15 g |
| Polymer of Example 1 | 2 g |
| Tertiary stearyl amine polyoxyethylenated with 5 moles of ethylene oxide | 1.5 g |
| Lactic acid, q.s.p. | pH 4.5 |
| Water, q.s.p. | 100 cc |

When applied to the hair, this clear solution produces a mild and abundant foam which is easily removed by rinsing. The hair is very easily untangled and after drying exhibits a puffed appearance and liveliness while remaining soft and easy to style.

3. The following shampoo composition is prepared:

| | |
|---|---|
| $C_{11}$–$C_{14}$ α-diol condensed with 3–4 moles of glycidol | 17 g |
| Polymer of Example 12 | 3 g |
| Lactic acid, q.s.p. | pH 3.5 |
| Water, q.s.p. | 100 cc |

When applied to the head, this clear solution produces a sufficiently mild and abundant foam and improves the untangling of wet hair. After drying, the hair is soft, shiny and has a light appearance.

Example VIII

Antipellicular Untangling Lotions

1. The following solution is prepared:

| | |
|---|---|
| Bis-(2-pyridyl-1-oxide) magnesium disulfide, sold under the name "Omadine MDS" | 0.5 g |
| Polymer of Example 1 | 0.7 g |
| Copolymer of vinylpyrrolidone/vinyl acetate, 70/30, K value (1% ethanol solution) = 30–50 | 1 g |
| KOH, q.s.p. | pH 5.5 |
| Water, q.s.p. | 100 cc |

When applied to the hair, this lotion, in addition to its antipellicular activity, facilitates the untangling of the hair.

2. The following lotion is prepared:

| | |
|---|---|
| (4-ethyl-benzyl alkyl dimethyl) ammonium chloride, wherein the alkyl moiety is a $C_{12}$–$C_{14}$–$C_{16}$–$C_{18}$ mixture | 1 g |
| Polymer of Example 1 | 0.7 g |
| Copolymer of vinylpyrrolidone/vinyl acetate, 70/30, K value (1% ethanol solution) = 30–50 | 1 g |
| KOH, q.s.p. | pH 5.5 |
| Water, q.s.p. | 100 cc |

The application of this lotion, which causes a significant reduction of pellicles after a few weeks, also provides easy untangling of the hair.

Example IX

Daily Anti-dandruff Untangling Lotions
The following lotion is prepared:

| | |
|---|---|
| Carboxy methyl cysteine | 0.3 g |
| Polymer of Example 7 | 0.6 g |
| Cationic polyglucosic derivative sold under the name "781568" by National Starch | 0.3 g |
| Ethyl alcohol | 50° |
| KOH, q.s.p. | Ph 7 |
| Water, q.s.p. | 100 cc |

When applied daily to greasy hair, this lotion not only improves the appearance of the hair but makes it easy to style and comb.

Example X

Oxidation Hair Dye Cream Support
1. The following cream is prepared:

| | |
|---|---|
| Cetyl stearyl alcohol | 22 g |
| Oleic diethanolamide | 5 g |
| Sodium cetyl stearyl sulfate | 4 g |
| Polymer of Example 105 | 6 g |
| Ammonia (11N) | 12 cc |
| M-diamino anisol sulfate | 0.048 g |
| Resorcin | 0.420 g |
| M-amino phenol base | 0.150 g |
| Nitro-p-phenylene diamine | 0.085 g |
| P-toluylene diamine | 0.004 g |
| Trilon B (see Example II, 1) | 1.000 g |

| | |
|---|---|
| Sodium bisulfite, d = 1.32 | 1.200 g |
| Water, q.s.p. | 100 g |

30 g of this cream are mixed with 45 g of H₂O₂ (20 volumes) thus producing a glossy, thick, pleasant to apply cream which adheres well to the hair. The cream is permitted to remain in contact with the hair for 30 minutes, after which the hair is rinsed and dried. When so applied to 100% white hair, a blond coloration is obtained. The hair, wet or dry, is easy to untangle and it has a shiny appearance and a pleasant and silky feel.

Essentially the same results are obtained by replacing the polymer of Example 105 with one of the polymers of the following examples:

| | |
|---|---|
| EX 106 | 5% |
| EX 107 | 5% |
| EX 108 | 6% |
| EX 110 | 4.5% |
| EX 111 | 6% |
| EX 76 | 3% |

2. The following cream is prepared:

| | |
|---|---|
| Stearyl alcohol | 18 g |
| Monoethanolamide of coco | 6 g |
| Ammonium lauryl sulfate (20% fatty alcohol) | 10 g |
| Polymer of Example 119 | 4 g |
| Ammonia, 22° Bé(11N) | 10 cc |
| M-diamino anisol sulfate | 0.048 g |
| Resorcin | 0.420 g |
| M-amino pheno base | 0.150 g |
| Nitro-p-phenylene diamine | 0.085 g |
| P-toluylene diamine | 0.004 g |
| Trilon B (see Ex. II, 1) | 1.000 g |
| Sodium bisulfite, d = 1.32 | 1.200 g |
| Water, q.s.p. | 100 g |

30 g of this cream are mixed with 45 g of H₂O₂ (20 volumes) thus producing a glossy, thick and pleasant to apply cream which adheres well to the hair. The cream is permitted to remain in contact with the hair for 30 minutes, after which the hair is rinsed and dried. When so applied to 100% white hair, a blond coloration is achieved. The hair, wet or dry, is easy to untangle and it has a shiny appearance and a pleasant and silky feel.

The same results are obtained by replacing the polymer of Example 119 by one of the polymers of the following examples:

| | |
|---|---|
| EX 75 | 5% |
| EX 104 | 4% |
| EX 102 | 5% |
| EX 81 | 5.5% |
| EX 103 | 6% |

Example XI

Dye Shampoo Compositions

1. The following dye shampoo composition is prepared:

| | |
|---|---|
| Nonyl phenol oxyethylenated with 4 moles of ethylene oxide | 25 g |
| Nonyl phenol oxyethylenated with 9 moles of ethylene oxide | 23 g |
| Polymer of Example 89 | 4 g |
| Ethyl alcohol (96%) | 7 g |
| Propylene glycol | 14 g |
| Ammonia, 22° Bé(11N) | 10 cc |
| M-diamino anisol sulfate | 0.030 g |
| Resorcin | 0.400 g |
| M-amino phenol base | 0.150 g |
| P-amino phenol base | 0.087 g |
| Nitro p-phenylene diamine | 1.000 g |
| Trilon B (see EX II, 1) | 3.000 g |
| Sodium bisulfite, d = 1.32 | 1.200 g |
| Water, q.s.p. | 100 g |

50 g of this composition are mixed with the same quantity of H₂O₂ (20 volumes) and the resulting gel is applied to the hair with a brush. The gel is permitted to remain in contact with the hair for 30 minutes, after which the hair is rinsed. The hair is easily untangled and has a silky feel. The hair is then set and dried. The hair is shiny and lively, has body, has a silky feel and combs easily. When so applied to deep brown hair, a chestnut coloration is obtained.

Example XII

Hair Treating Lotion (Application With Rinsing)

30 ml of the following solution are applied to wet, clean hair:

| | |
|---|---|
| Polymer of Example 94 | 5 g |
| Monoethanolamine, q.s.p. | pH 7.5 |
| Water, q.s.p. | 100 cc |

This lotion is permitted to remain in contact with the hair for 5 minutes after which the hair is rinsed. The hair has a soft feel and is easily untangled. The hair is then set and dried. The dry hair combs easily, is shiny and lively and has body.

The same results are obtained by replacing the polymer of Example 94 by one of the polymers of the following examples:

| | |
|---|---|
| EX 91 | 4 g |
| EX 78 | 6 g |
| EX 93 | 6 g |
| EX 100 | 4 g |
| EX 97 | 6 g |
| EX 112 | 5 g |
| EX 96 | 5 g |
| EX 98 | 6.5 g |
| EX 101 | 4.5 g |
| EX 99 | 5 g |

Example XIII

Hair Restructuring Lotion (Application With Rinsing)

1. Before use, 2 g of N,N'-di-(hydroxymethyl) ethylene thiourea are mixed with 25 cc of the following solution:

| | |
|---|---|
| Polymer of Example 117 | 5 g |
| HCl, q.s.p. | pH 2.5 |
| Water, q.s.p. | 100 cc |

This mixture is applied to washed and dried hair and is permitted to remain in contact therewith for 10 minutes, after which the hair is rinsed. The hair is easy to untangle and has a silky feel. The hair is then set and dried under a hood. The dry hair is easy to comb, is shiny and lively and has body.

2. Before use, 2 g of N,N'-di-(hydroxymethyl) ethylene thiourea are mixed with 25 cc of the following solution:

| Polymer of Example 79 | 3 g |
| HCl, q.s.p. | pH 2.5 |
| Water, q.s.p. | 100 cc |

This mixture is applied to washed and dried hair and is permitted to remain in contact therewith for 10 minutes, after which the hair is rinsed. The hair is easy to untangle and has a silky feel. The hair is then set and dried under a hood. The dry hair is easy to comb, is lively and has body.

3. Before use, 2 g of N,N'-di-(hydroxymethyl) ethylene thiourea are mixed with 25 cc of the following solution:

| Polymer of Example 109 | 4 g |
| HCl, q.s.p. | pH 2.5 |
| Water, q.s.p. | 100 cc |

This mixture is applied to washed and dried hair and is permitted to remain in contact therewith for 10 minutes, after which the hair is rinsed. The hair is easy to untangle and has a silky feel. The hair is then set and dried under a hood. The dry hair is easy to comb, is shiny and lively and has body.

Example XIV

Hair Restructuring Lotion—Application Without Rinsing

Before use, 0.3 g of N,N'-di-(hydroxymethyl) ethylene thiourea is mixed with 25 cc of the following solution:

| Polymer of Example 82 | 0.5 g |
| Phosphoric acid, q.s.p. | pH 2.8 |
| Water, q.s.p. | 100 cc |

This mixture is applied to washed and dried hair before being set. The hair combs easily and has a silky feel. The hair is then set and dried. The hair is shiny and lively, has body, has a silky feel and combs easily.

The same result is obtained by replacing the polymer of Example 82 by one of the polymers of the following examples:

| EX 77 | 0.5 g |
| EX 87 | 0.6 g |
| EX 83 | 0.6 g |
| EX 88 | 0.5 g |

Example XV

Hair Setting Lotion for Sensitized Hair

1. The following hair setting lotion is prepared:

| Polyvinylpyrrolidone, MW 40,000 | 1 g |
| Polymer of Example 92 | 2.5 g |
| Ethyl alcohol, q.s.p. | 100 cc |

The above lotion is applied to hair and thereafter the hair is set and dried. The hair is hard and plasticized, is shiny and has body. The hair also has a silky feel and combs easily.

The same result is obtained by replacing the polymer of Example 92 by the following polymer:

| Polymer of Example 120 | 2% |

2. The following hair setting lotion is prepared:

| Polyvinylpyrrolidone, MW 40,000 | 1 g |
| Polymer of Example 85 | 1 g |
| Ethyl alcohol, q.s.p. | 100 cc |

The above lotion is applied to the hair, after which the hair is set and dried. The hair is hard and plasticized, is shiny and has body. The hair also has a silky feel and combs easily.

The same results are obtained by replacing the polymer of Example 85 by the following product:

| Polymer of Example 84 | 1.2 g |

3. The following hair setting lotion is prepared:

| Polyvinylpyrrolidone, MW 40,000 | 1 g |
| Polymer of Example 86 | 0.8 g |
| Ethyl alcohol, q.s.p. | 100 cc |

The above lotion is applied to the hair, after which the hair is set and dried. The hair is hard and plasticized, is shiny and has body. The hair also has a silky feel and is easy to comb.

Example XVI

Pre-shampoo Compositions 10 g of the following solution are applied to dirty, dry hair:

| Polymer of Example 1 | 2 g |
| Monoethanolamine, q.s.p. | pH 7 |
| Water, q.s.p. | 100 cc |

The solution is permitted to remain in contact with the hair for 10 minutes, after which the hair is given an anionic shampoo in two stages. Untangling of the wet hair is facilitated and the hair is soft. After setting and drying, the hair combs easily, has a soft feel and is shiny and lively. This same solution can be packaged as an aerosol.

Example XVII

Pre-shampoo Composition 15 g of the following solution are applied to dry, dirty hair:

| Polymer of Example 13 | 1 g |
| Polymer of Example 17 | 1 g |
| Monoethanolamine, q.s.p. | pH 7 |
| Water, q.s.p. | 100 cc |

The solution is permitted to remain in contact with the hair for 2 minutes after which the hair is given an anionic shampoo in two stages. The wet hair is easily untangled and is soft. After setting and drying, the hair is easily combed, has a soft feel and is shiny and lively. This same solution can be packaged in an aerosol container together with a propellant such as nitrogen, nitrous oxide or a halogenated hydrocarbon including dichlorodifluoromethane or trichloromonofluoromethane and the like.

Example XVIII

Pre-dyeing Treating Lotion 20 cc of the following solution are applied to dry, dirty hair:

| Polymer of Example 1 | 3 g |
|---|---|
| Monoethanolamine, q.s.p. | pH 8 |
| Water, q.s.p. | 100 g |

This solution is permitted to remain in contact with the hair for 5 minutes, after which the hair is given an ammoniacal oxidation dye treatment wherein the dye composition is permitted to remain in contact with the hair for 30 minutes. After rinsing and being given an anionic shampoo, the hair is very easily untangled. After setting and drying, the hair is silky, shiny, lively and easy to style.

Example XIX

An anionic shampoo composition is prepared as follows:

| Triethanolamine lauryl sulfate | 10 g |
|---|---|
| Polymer of Example 17 | 1 g |
| Triethanolamine, q.s.p. | pH 8 |
| Water, q.s.p. | 100 g |

Example XX

A pre-shampoo composition is prepared as follows:

| Polymer of Example 17 | 2 g |
|---|---|
| Monoethanolamine, q.s.p. | pH 7 |
| Water, q.s.p. | 100 g |

Ten grams of this composition are applied to dry, dirty hair and the composition is permitted to remain in contact therewith for 2 minutes, after which the hair is given a conventional anionic shampoo. The hair, wet or dry, is easy to untangle and has a soft feel.

Analogous results are obtained by replacing the polymer of Example 17 by the polymers of Examples 1, 7, 13, 20, 22, 23, 46, 75, 76, 91, 92, 93, 105, 108, 110, 111, 112, 117, 123, 130, 136 and 140.

Analogous pre-shampoo compositions have been prepared as aerosol formulations using the same polymers. Such a formation can be produced in the following manner:

| Polymer of Example 17 | 8 g |
|---|---|
| Monoethanolamine, q.s.p. | pH 7 |
| Water, q.s.p. | 100 g |

25 g of this solution are introduced into an aerosol container. Nitrogen is introduced into the container until there is obtained a pressure of 12 kg/cm$^2$.

With the use of the aerosol thus obtained, dry hair to be washed is impregnated with the composition which is permitted to remain in contact with the hair for a few minutes. The hair is then given a conventional anionic shampoo.

Example XXI

Pre-shampoo Composition in the form of an Aerosol Foam

The following aerosol composition is prepared:

| Sodium cetyl stearyl sulfate | 1.3 g |
|---|---|
| Nonyl phenol oxyethylenated with 4 moles of ethylene oxide | 2.5 g |
| Nonyl phenol oxyethylenated with 9 moles of ethylene oxide | 1.5 g |
| Polymer of Example 17 | 3.0 g |
| Mixture of Freon-114 and Freon-12 (70:30) | 10.0 g |
| Filling rate - 65% | |

This composition is applied to dry, dirty hair by rubbing in order to get good penetration of the foam into the hair. A conventional anionic shampoo is then given and the materials applied to the hair are permitted to remain in contact with the hair for 2 to 3 minutes, after which the hair is rinsed. The hair has a soft feel and untangles easily.

The hair is then set and dried. The dry hair combs easily, is shiny and lively and has body.

Example XXII

Oxidation Hair Dye Composition

As in Example X, an oxidation hair dye component is admixed with a quaternized component to produce an oxidation hair dye cream support, which in turn is admixed with $H_2O_2$, an oxidizing agent to produce a hair dye composition.

In this Example the oxidation hair dye component comprises an admixture of the following ingredients:

| Cetyl stearyl alcohol | 22 g |
|---|---|
| Oleic diethanolamide | 5 g |
| Sodium cetyl stearyl sulfate | 4 g |
| Ammonia (11N) | 12 cc |
| M-diamino anisol sulfate | 0.048 g |
| Resorcin | 0.420 g |
| M-amino phenol base | 0.150 g |
| Nitro-p-phenylene diamine | 0.085 g |
| P-toluylene diamine | 0.004 g |
| Trilon B (see Example II, 1) | 1.000 g |
| Sodium bisulfite, d = 1.32 | 1.200 g |
| Water, q.s.p. | 100 g |

To 55 g of this oxidation hair dye component there are added 5 g of a polymer of Example 105, provided as before from a distinct source. To 60 g of the resulting mixture there are added 90 g of $H_2O_2$ (20 volumes) also, as before, from a distinct source. The resulting admixture is a glossy, thick, pleasant to apply cream which adheres well to the hair. The cream is permitted to remain in contact with the hair for 30 to 40 minutes, after which the hair is rinsed and dried. When so applied to 100% white hair, a blond coloration is obtained.

The hair, wet or dry, is easy to untangle and it has a shiny appearance and a pleasant and silky feel.

Example XXIII

Permanent Wave Composition

As mentioned above, the polymers of formula I may be employed in permanent waving compositions.

It is known that standard techniques for giving a permanent waving to the hair consists, in a first stage, in making an opening of the S-S bonds of the hair keratin with a composition containing a reducing agent, and then, preferably after having rinsed the hair, reconstituting in a second stage said S-S bonds by applying to the hair, subjected to an extension, an oxidizing composition to give the desired shape to the hair.

The formulation of said reducing and oxidizing composition is known and described in cosmetology books, such as "Problèmes capillaires", by E. SIDI and C. ZVIAK, Paris, 1966 (Gauthier-Villard).

An example of a permanent waving composition is described below:

A permanent waving operation is carried out by applying on the hair the following reducing composition:

| | |
|---|---|
| Thioglycolic acid | 8.0 g |
| Ammonia, q.s.p. | pH = 7 |
| Ammonium bicarbonate | 6.4 g |
| Dimethyl distearylammonium chloride | 0.2 g |
| Polymer of Example 1 | |
| Oleic alcohol oxyethylenated with 20 moles of ethylene oxide | 1.0 g |
| Perfume, q.s., | |
| Water, q.s.p. | 100 g |

The hair is then waved on rollers, and after 5-15 minutes, is carefully rinsed with water. Then, the following oxidising composition is applied:

| | |
|---|---|
| Dimethyldistearyl ammonium chloride | 0.3 g |
| Phenacetin | 0.1 g |
| Citric acid | 0.3 g |
| Nonylphenol oxyethylenated with 9 moles ethylene oxide | 1.0 g |
| Hydrogen peroxide, q.s.p. | 8 volumes |
| Coloring agent, q.s. | |
| Perfume, q.s. | |
| Water q.s.p. | 100 g |

After 10 minutes, the hair is rinsed and dried. The wet hair is easily untangled and has a silky feel. The dry hair is shiny and lively, has a silky feel and is easy to untangle.

Example XXIV

Hair Bleaching Composition

As mentioned above, the polymers of formula I overcome the drawbacks of hair being sensitized by treatments such as bleaching.

It is known that standard techniques for bleaching hair consist in oxidizing the pigments of hair with an oxidizing agent such as $H_2O_2$, persulfates, etc . . . in alkaline medium.

The formulation of bleaching compositions is known and described in cosmetology books, such as "Problèmes Capillaires", by E. SIDI and C. ZVIAK, Paris, 1966 (Gauthier-Villard).

An example of a bleaching composition is given below:

| | |
|---|---|
| Oleic acide | 20.0 g |
| Monoethanolamine | 7.0 g |
| Oleic alcohol | 12.0 g |
| Triethanolamine lauryl sulfate (40% active material) | 3.0 g |
| MERGITAL OC 30* | 3.0 g |
| Lauric diethanolamide | 12.0 g |
| Polymer of Example 1 | 3.0 g |
| Butylglycol | 5.0 g |
| Ethyl alcohol | 8.5 g |
| Propylene glycol | 6.0 g |
| Trilon B | 0.2 g |
| ammonia 22° Be | 18 ml |
| Water q.s.p. | 100 g |

*MERGITAL OC 30 is a trade name for oleocetylic alcohol oxyethylenated with 30 moles ethylene oxide, sold by Henkel.

60 g of said composition are mixed with 120 g of a 20 volumes hydrogen peroxide solution. A gelified liquid is obtained, which is easily applied with a brush. After 30-45 minutes, the hair is rinsed.

The wet hair is easy to untangle, and has a silky feel.

After drying, the hair is shiny, lively, and has body; the feel is silky and untanglingis easy. The state of the hair is improved as compared with hair treated with the same composition but without the polymer of Example 1.

By application on dark brown hair, a dark blond coloration is obtained.

What is claimed is:

1. A process for treating the skin comprising applying to the skin a cosmetic composition in an amount sufficient to impart a soft feeling to the skin and to assist in the hydration thereof, said cosmetic composition comprising in gel or emulsion form an aqueous phase and an emulsified oil phase, said aqueous phase containing in solution a quaternized polymer having recurring units of the formula

wherein

R is lower alkyl or —CH$_2$—CH$_2$OH;

R' is alkyl, cycloalkyl or aralkyl containing a maximum of 20 carbon atoms, or R and R' together with the nitrogen atom to which they are attached form a heterocycle capable of containing a heteroatom other than nitrogen;

A is a divalent group selected from o-, m- or p-xylylidene of the formula  (1)

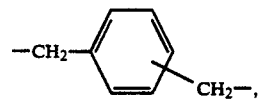

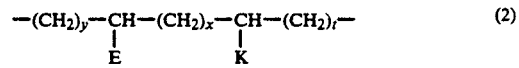  (2)

wherein x, y and t are whole numbers ranging from 0 to 11 such that the sum (x+y+t) is greater than or equal to 0 and lower than 18, and E and K represent hydrogen or alkyl having less than 18 carbon atoms, —(CH$_2$)$_n$—S—(CH$_2$)$_n$—, (3)

—(CH$_2$)$_n$—O—(CH$_2$)$_n$—, (4)

—(CH$_2$)$_n$—S—S—(CH$_2$)$_n$—, (5)

—(CH$_2$)$_n$—SO—(CH$_2$)$_n$—, (6)

—(CH$_2$)$_n$—SO$_2$—(CH$_2$)$_n$— and (7)

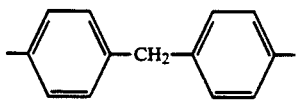
(8)

wherein n is equal to 2 or 3;
B represents a divalent group selected from o-, m- or p-xylylidene of the formula (1)

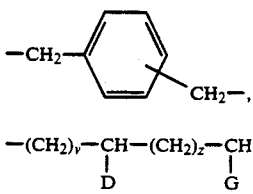

—(CH$_2$)$_v$—CH—(CH$_2$)$_z$—CH—(CH$_2$)$_u$— (2)
　　　　　|　　　　　　　|
　　　　　D　　　　　　　G wherein D and G represent hydrogen or alkyl having less than 18 carbon atoms and v, z and u are whole numbers ranging from 0 to 11, with two of v, z and u simultaneously being capable of being 0, such that the sum (v+z+u) is greater than or equal to 1 and lower than 18 and such that the sum (v+z+u) is greater than 1 when the sum (x+y+t) is equal to 0, OH
　　　|
—CH$_2$—CH—CH$_2$—and (3)

—(CH$_2$)$_n$—O—(CH$_2$)$_n$— (4)

wherein n is 2 or 3; and
X$^\ominus$ is an anion derived from an organic or mineral acid, said polymer being present in an amount between 0.25 and 10 percent by weight of said composition.

2. The process of claim 1 wherein A is selected from o-, m- or p-xylylidene of the formula (1)

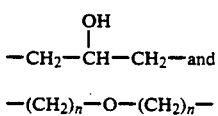

—(CH$_2$)$_y$—CH—(CH$_2$)$_x$—CH—(CH$_2$)$_t$— (2)
　　　　　|　　　　　　　|
　　　　　E　　　　　　　K wherein E, K, x, y and t have the meanings given in claim 1 and
B is selected from o-, m- or p-xylylidene of the formula (1)

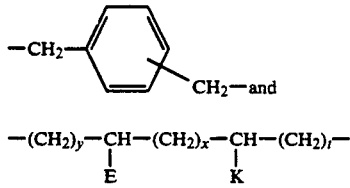

—(CH$_2$)$_v$—CH—(CH$_2$)$_z$—CH—(CH$_2$)$_u$— (2)
　　　　　|　　　　　　　|
　　　　　D　　　　　　　G wherein D, G, v, z and u have the meanings given in claim 1.

3. The process of claim 1 wherein
R is methyl or hydroxyethyl,
R' is alkyl having 1-16 carbon atoms, benzyl or cyclohexyl, or R and R' represent a polymethylene having 2-6 carbon atoms or —(CH$_2$)$_2$—O—(CH$_2$)$_2$;
A is xylylidene, polymethylene having 2-12 carbon atoms, polymethylene having 2-12 carbon and being branched by one or two alkyl substituents having 1-12 carbon atoms,

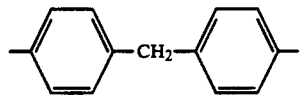

—(CH$_2$)$_n$—S—(CH$_2$)$_n$—, —(CH$_2$)$_n$—O—(CH$_2$)$_n$,
—(CH$_2$)$_n$—S—S—(CH$_2$)$_n$, —(CH$_2$)$_n$—SO—(CH$_2$)$_n$ or —(CH$_2$)$_n$—SO$_2$—(CH$_2$)$_n$;

B is polymethylene having 3-10 carbon atoms, polymethylene having 3-10 carbon atoms and being branched by one or two alkyl substituents having 1-12 carbon atoms, xylylidene, —CH$_2$—CHOH—CH$_2$— or —(CH$_2$)$_n$—O—(CH$_2$)$_n$; and
x is chlorine, bromine or iodine.

4. The process of claim 1 wherein
R is methyl;
R' is alkyl having 1-16 carbon atoms, benzyl or cyclohexyl, or R and R' together represent —(CH$_2$)$_2$—O—(CH$_2$)$_2$;
A is xylylidene, polymethylene having 2-12 carbon atoms, or polymethylene having 2-12 carbon and being branched by one or two alkyl substituents having 1-12 carbon atoms,
B is polymethylene having 3 to 10 carbon atoms, polymethylene having 3 to 10 carbon atoms and being branched by one or two alkyl substituents having 1-12 carbon atoms or xylylidene; and
X is chlorine, bromine or iodine.

5. The process of claim 1 wherein R=R'=CH$_3$, X=Br and A and B are selected from the combinations of (1) A represents —CH$_2$—CH—(CH$_2$)$_5$—CH—CH$_2$—or
　　　|　　　　　　　|
　　　C$_4$H$_9$　　　　　C$_4$H$_9$ —CH$_2$—CH—CH$_2$—and
　　　|
　　　C$_{12}$H$_{25}$ B represents (CH$_2$)$_3$;
(2) A represents (CH$_2$)$_2$ and B represents (CH$_2$)$_4$, (CH$_2$)$_6$, (CH$_2$)$_{10}$ or

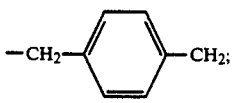

(3) A represents $(CH_2)_6$ and
B represents $(CH_2)_3$, $(CH_2)_4$, $(CH_2)_5$, $(CH_2)_6$, $(CH_2)_{10}$,

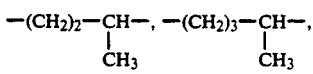

o-xylylidene or p-xylylidene;

(4) A represents $(CH_2)_5$ and
B represents $(CH_2)_7$ or $(CH_2)_9$; and (5) A represents $(CH_2)_{10}$ and
B represents $(CH_2)_4$ or $(CH_2)_{10}$.

6. The process of claim 1 wherein R and R' together represent $-(CH_2)_2-O-(CH_2)_2-$, X represents Br and A and B are selected from the combinations of (1) A represents $(CH_2)_6$ or $(CH_2)_{10}$ and
B represents $(CH_2)_3$; and (2) A represents $(CH_2)_3$ and
B represents $(CH_2)_6$.

7. The process of claim 1 wherein $R=R'=CH_3$, $X=Cl$ and A and B are selected from the combinations of (1) A represents $(CH_2)_6$ and
B represents $-CH_2-CHOH-CH_2-$ or $-(CH_2)_2-o-(CH_2)_2-$, (2) A represents $(CH_2)_3$ and
B represents $-(CH_2)_2-O-(CH_2)_2-$, and (3) A represents $(CH_2)_3$ and
B represents $(CH_2)_6$.

8. The process of claim 1 wherein $R=R'=CH_3$, $X=Br$ and A and B are selected from the combinations of (1) A represents $(CH_2)_2-S-S-(CH_2)_2-$ and
B represents $(CH_2)_3$, $(CH_2)_4$, $(CH_2)_5$, $(CH_2)_6$, $(CH_2)_{10}$, $CH_2-CHOH-CH_2$, $(CH_2)_2-O-(CH_2)_2$ or p-xylylidene;

(2) A represents $(CH_2)_3-O-(CH_2)_3$, $(CH_2)_3-S-S-(CH_2)_3$, $(CH_2)_2-S-(CH_2)_2$, $(CH_2)_2-SO-(CH_2)_2$ or

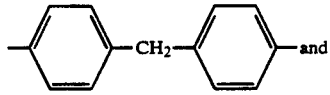

B represents $(CH_2)_3$;

(3) A represents $(CH_2)_2-O-(CH_2)_2$ and
B represents p-xylylidene, $(CH_2)_2-O-(CH_2)_2$ or $-CH_2-CHOH-CH_2$;

(4) A represents $(CH_2)_3$, $(CH_2)_4$, $CH_2)_5$, $(CH_2)_6$, $(CH_2)_{10}$ or p-xylylidene, and
B represents $CH_2-CHOH-CH_2$; and (5) A represents $(CH_2)_2-SO_2-(CH_2)_2$ and
B represents $(CH_2)_6$.

9. The process of claim 1 wherein $R=CH_3$, $R'=C_4H_9$ and A and B are selected from the combinations of (1) A represents $(CH_2)_2-S-S-(CH_2)_2$ and
B represents m-xylylidene;

(2) A represents $(CH_2)_{10}$ and
B represents $CH_2-CHOH-CH_2$; and (3) A represents p-xylylidene and
B represents $(CH_2)_2-O-(CH_2)_2$.

10. The process of claim 1 wherein $R=CH_3$, $R'=C_8H_{17}$ and A and B are selected from the combinations of (1) A represents $(CH_2)_2-S-S-(CH_2)_2$ and
B represents $(CH_2)_3$;

(2) A represents $(CH_2)_6$ and
B represents $(CH_2)_2-O-(CH_2)_2$.

11. The process of claim 1 wherein $R=CH_3$, $R'=C_{12}H_{25}$ and A and B are selected from the combinations of (1) A represents $(CH_2)_2-S-S-(CH_2)_2$ and
B represents $(CH_2)_6$; and (2) A represents $(CH_2)_3$ and
B represents $(CH_2)_2-O-(CH_2)_2$.

12. The process of claim 1 wherein $R=-CH_2-CH_2OH$, $R'=CH_3$ and A and B are selected from the combinations of (1) A represents $(CH_2)_3$ and
B represents $(CH_2)_6$, $(CH_2)_{10}$ or $-CH_2-CHOH-CH_2-$; and (2) A represents m-xylylidene, and
B represents $(CH_2)_6$.

13. The process of claim 1 wherein $R=-CH_2-CHOH$, $R'=C_4H_9$, $A=(CH_2)_6$ and $B=(CH_2)_2-o-(CH_2)_2$.

14. The process of claim 1 wherein $R=-CH_2-CHOH$, $R'=C_8H_{17}$, $A=(CH_2)_3$ and $B=$p-xylylidene or $-CH_2-CHOH-CH_2-$.

15. The process of claim 1 wherein $R=-CH_2-CHOH$, $R'=C_{12}H_{25}$, $A=(CH_2)_6$ and $B=(CH_2)_3$.

16. The process of claim 1 wherein R and R' together represent $-(CH_2)_2-o-(CH_2)_2-$ or $-(CH_2)_5-$, $A=(CH_2)_6$ and $B=-CH_2-CHOH-CH_2-$.

17. The process of claim 1 wherein $R=R'=CH_3$, $X=Br$ and A and B are selected from the combinations of (1) A represents $(CH_2)_4$ and
B represents $(CH_2)_7$, $(CH_2)_9$ or o-xylylidene;

(2) A represents $(CH_2)_5$ and
B represents

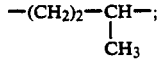

(3) A represents $(CH_2)_2-O-(CH_2)_2$ and
B represents $(CH_2)_3$;

(4) A represents

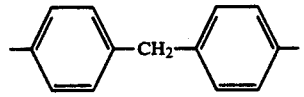

and
B represents $(CH_2)_2-o-(CH_2)_2$ or $-CH_2-CHOH-CH_2$ and (5) A represents p-xylylidene, and
B represents $CH_2-CHOH-CH_2$.

18. The process of claim 1 wherein $R=CH_3$, $R'=$n-propyl, $x=Br$ and A and B are selected from the combinations of (1) A represents $(CH_2)_3$ and
B represents $(CH_2)_4$;

(2) A represents $(CH_2)_6$ and
B represents

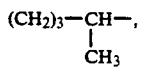

o-xylylidene or $(CH_2)_4$; and
(3) A represents m-xylylidene, and
B represents $(CH_2)_{10}$.

19. The process of claim 1 wherein $R=CH_3$, $R'=$isopropyl, $X=Br$, $A=(CH_2)_3$ and $B=(CH_2)_3$ or $(CH_2)_7$.

20. The process of claim 1 wherein $R=CH_3$, $R'=$benzyl, $B=CH_2-CHOH-CH_2$ and $A=(CH_2)_3$ when $X=Br$ or $A=(CH_2)_6$ when $X=Cl$.

21. The process of claim 1 wherein $R=CH_3$, $R'=C_4H_9$, $X=Br$, $A=$m-xylylidene and $B=CH_2-CHOH-CH_2$.

22. The process of claim 1 wherein R and R' together represent $-(CH_2)_5-$, $X=Br$, $B=CH_2-CHOH-CH_2$ and $A=(CH_2)_2$

or m-xylylidene.

23. A process for treating the skin comprising applying to the skin a composition comprising in a cosmetically acceptable vehicle suitable for application to the skin a quaternized polymer having recurring units of the formula

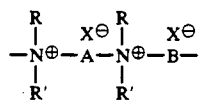

wherein
R is lower alkyl or $-CH_2-CH_2OH$;
R' is alkyl, cycloalkyl or aralkyl containing a maximum of 20 carbon atoms, or R and R' together with the nitrogen atom to which they are attached form a heterocycle capable of containing a heteroatom other than nitrogen;
A is a divalent group selected from o-, m- or p-xylylidene of the formula (1)

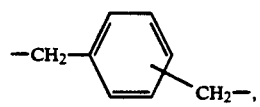

$-(CH_2)_y-\underset{\underset{E}{|}}{CH}-(CH_2)_x-\underset{\underset{K}{|}}{CH}-(CH_2)_t-$ (2)

wherein x, y and t are whole numbers ranging from 0 to 11 such that the sum $(x+y+t)$ is greater than or equal to 0 and lower than 18, and E and K represent hydrogen or alkyl having less than 18 carbon atoms,

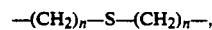

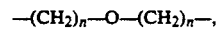

$-(CH_2)_n-S-S-(CH_2)_n-$, (5)

$-(CH_2)_n-SO-(CH_2)_n-$, (6)

$-(CH_2)_n-SO_2-(CH_2)_n-$ and (7)

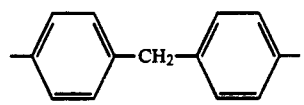  (8)

wherein n is equal to 2 or 3;
B represents a divalent group selected from o-, m- or p-xylylidene of the formula (1)

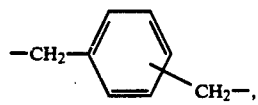

$-(CH_2)_v-\underset{\underset{D}{|}}{CH}-(CH_2)_z-\underset{\underset{G}{|}}{CH}-(CH_2)_u-$ (2)

o-, m- or p-xylylidene of the formula (1)

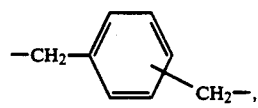

$-(CH_2)_v-\underset{\underset{D}{|}}{CH}-(CH_2)_z-\underset{\underset{G}{|}}{CH}-(CH_2)_u-$ (2)

wherein D and G represent hydrogen or alkyl having less than 18 carbon atoms and v, z and u are whole numbers ranging from 0 to 11, with two of v, z and u simultaneously being capable of being 0, such that the sum $(v+z+u)$ is greater than or equal to 1 and lower than 18 and such that the sum $(v+z+u)$ is greater than 1 when the sum $(x+y+t)$ is equal to 0,

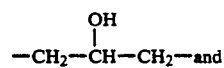 (3)

$-(CH_2)_n-O-(CH_2)_n-$ (4)

wherein n is 2 or 3; and
$X^\ominus$ is an anion derived from an organic or mineral acid, said quaternized polymer being present in an amount sufficient to impart a soft feeling to the skin and to assist in the hydration thereof.

24. The process of claim 23 wherein said quaternized polymer has recurring units of the formula

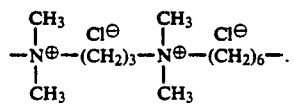

* * * * *

UNITED STATES PATENT AND TRADEMARK OFFICE
CERTIFICATE OF CORRECTION

PATENT NO. : 5,196,189

DATED : March 23, 1993

INVENTOR(S) : Bernard JACQUET et al

It is certified that error appears in the above-identified patent and that said Letters Patent is hereby corrected as shown below:

Cancel Claim 1 (Col. 46, line 30, to Col. 47, line 50).

Each of Claims 2 to 22, line 1, change "1" to --23--.

Signed and Sealed this

Third Day of May, 1994

*Attest:*

BRUCE LEHMAN

*Attesting Officer*  *Commissioner of Patents and Trademarks*